(12) United States Patent
Umeda et al.

(10) Patent No.: US 9,403,825 B2
(45) Date of Patent: Aug. 2, 2016

(54) COMPOUND, SOLAR CELL MODULE, AND PHOTOVOLTAIC POWER GENERATION DEVICE

(71) Applicant: Sharp Kabushiki Kaisha, Osaka (JP)

(72) Inventors: Tokiyoshi Umeda, Osaka (JP); Daisuke Tsukio, Osaka (JP); Yukio Takenaka, Osaka (JP)

(73) Assignee: Sharp Kabushiki Kaisha, Osaka (JP)

( * ) Notice: Subject to any disclaimer, the term of this patent is extended or adjusted under 35 U.S.C. 154(b) by 0 days.

(21) Appl. No.: 14/769,936

(22) PCT Filed: Feb. 24, 2014

(86) PCT No.: PCT/JP2014/054362
§ 371 (c)(1),
(2) Date: Aug. 24, 2015

(87) PCT Pub. No.: WO2014/132929
PCT Pub. Date: Sep. 4, 2014

(65) Prior Publication Data
US 2016/0002238 A1      Jan. 7, 2016

(30) Foreign Application Priority Data

Feb. 27, 2013   (JP) .................................. 2013-037938

(51) Int. Cl.
*C07D 471/22* (2006.01)
*H01L 31/00* (2006.01)
(Continued)

(52) U.S. Cl.
CPC ................ *C07D 471/22* (2013.01); *C09B 5/62* (2013.01); *C09K 11/06* (2013.01); *H01L 31/055* (2013.01);
(Continued)

(58) Field of Classification Search
USPC ....................... 546/27; 136/263, 252; 313/498
See application file for complete search history.

(56) References Cited

FOREIGN PATENT DOCUMENTS

JP        03-273686 A      12/1991

OTHER PUBLICATIONS

International Search Report and Written Opinion for corresponding International Application No. PCT/JP2014/054362 mailed Apr. 28, 2014.

(Continued)

*Primary Examiner* — Charanjit Aulakh
(74) *Attorney, Agent, or Firm* — Renner, Otto, Boisselle & Sklar, LLP

(57) ABSTRACT

This compound is represented by the following general formula (IA) or (IB) (in the formula, $R^1$ and $R^2$ are each independently a hydrogen atom, an alkyl group, an alkoxy group, an aryl group, or an aryloxy group, and a plurality of the $R^1$ and the $R^2$ may be the same as each other or different from each other; $R^3$ corresponds to a hydrogen atom or an alkyl group, and a plurality of $R^3$ may be the same as each other or different from each other). A solar cell module includes the compound. A photovoltaic power generation device includes the solar cell module.

[Chem. 1]

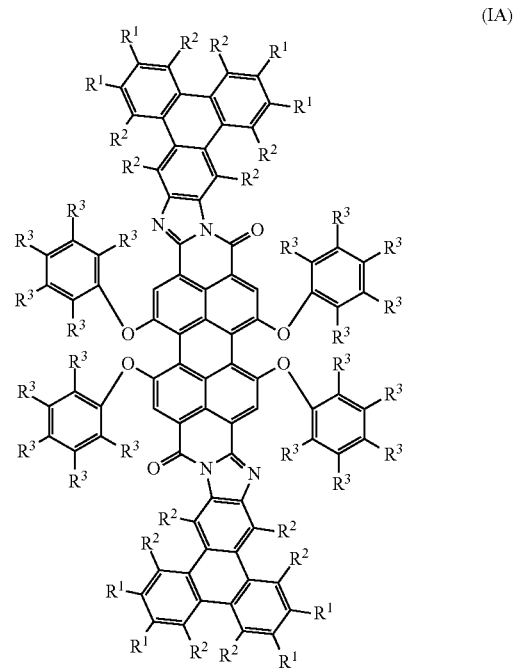

(IA)

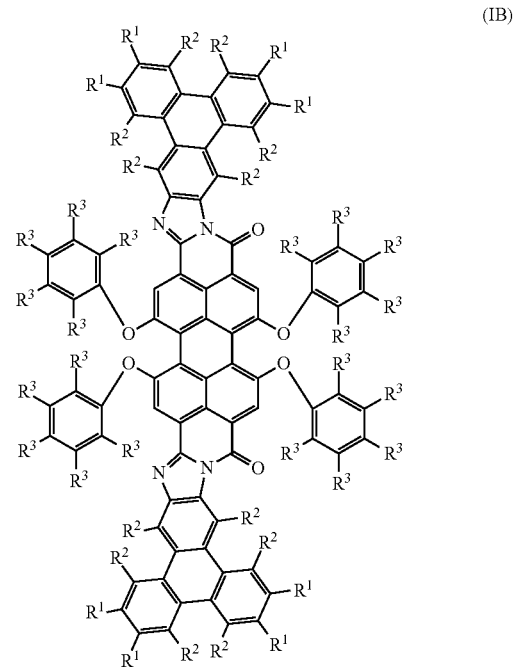

(IB)

7 Claims, 10 Drawing Sheets

(51) Int. Cl.
  H01L 51/00    (2006.01)
  C09B 5/62     (2006.01)
  C09K 11/06    (2006.01)
  H01L 31/055   (2014.01)
  H01L 51/44    (2006.01)
  H01L 51/42    (2006.01)
  H01L 31/0256  (2006.01)

(52) U.S. Cl.
  CPC ........ *H01L 51/0053* (2013.01); *H01L 51/0072* (2013.01); *H01L 51/44* (2013.01); *C09K 2211/1044* (2013.01); *H01L 51/4253* (2013.01); *H01L 2031/0344* (2013.01); *Y02E 10/549* (2013.01)

(56) References Cited

OTHER PUBLICATIONS

Michael G. Debije et al., Promising fluorescent dye for solar energy conversion based on a perylene perinone, Applied Optics, Jan. 7, 2011, vol. 50, No. 2, p. 163-169.

Heribert Quante et al., "Synthesis of Soluble Perylenebisamidine Derivatives. Novel Long-Wavelength Absorbing and Fluorescent Dyes", Chemistry of Materials, 1997, vol. 9, No. 2, p. 495-500.

Long Chen et al., "Noncovalently Netted, Photoconductive Sheets with Extremely High Carrier Mobility and Conduction Anisotropy from Triphenylene-Fused Metal Trigon Conjugates", J. Am. Chem. Soc., 2009, 131, 7287.

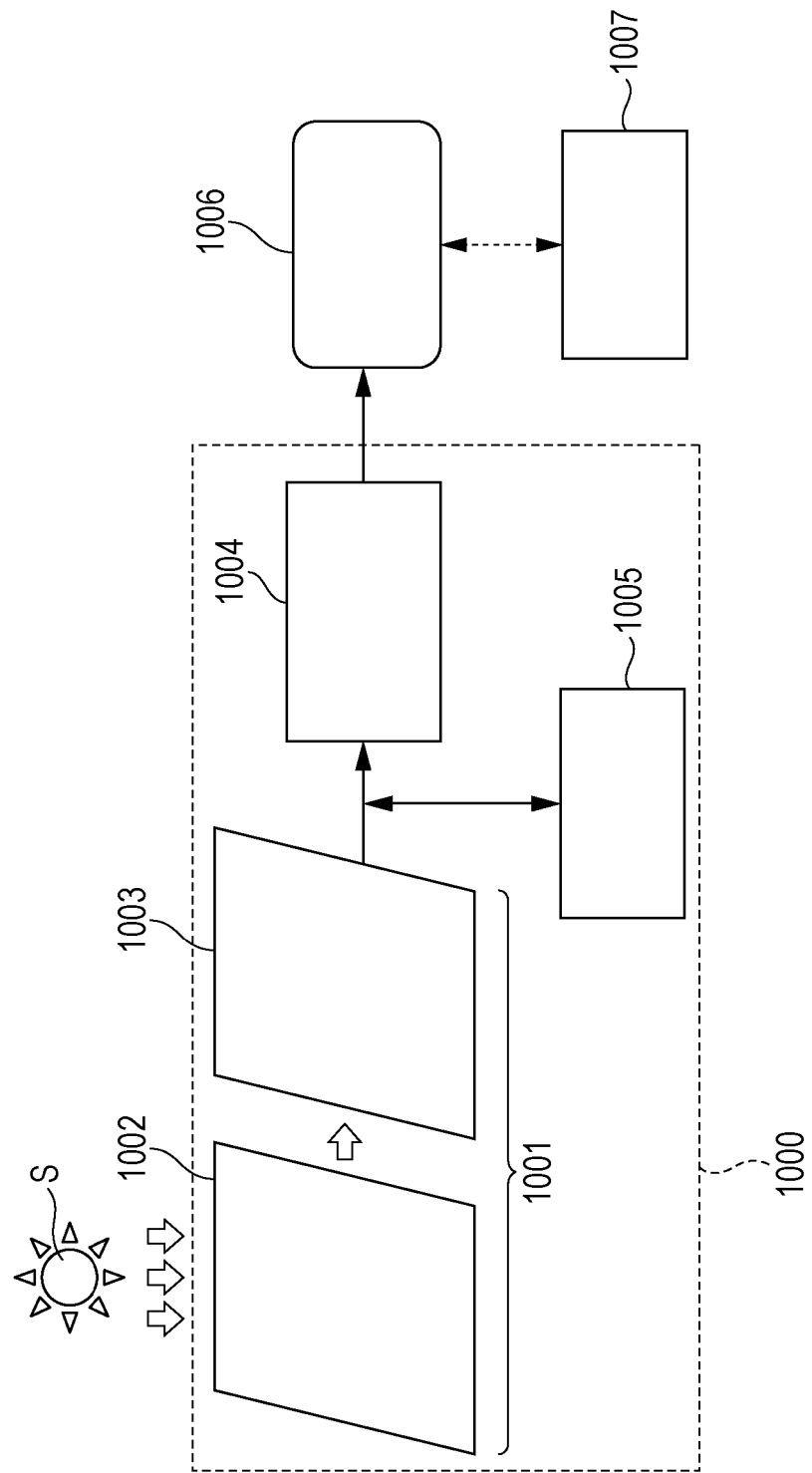

COMPOUND, SOLAR CELL MODULE, AND PHOTOVOLTAIC POWER GENERATION DEVICE

TECHNICAL FIELD

The present invention relates to a novel compound, a solar cell module using the compound, and a photovoltaic power generation device including the solar cell module.

The present application claims priority to Japanese Patent Application No. 2013-037938 filed in Japan on Feb. 27, 2013, the contents of which are incorporated herein by reference.

BACKGROUND ART

There is a large need for a compound (phosphor) which emits light in a near infrared region, in various fields, for example, a light concentration material and a wavelength conversion material in a photovoltaic power generation device, a material for a fluorescent probe in a living body, and the like.

As an example, a photovoltaic power generation device using such a phosphor will be described. A photovoltaic power generation device (solar energy collecting window) disclosed in PTL 1 is one of known photovoltaic power generation devices that generate electrical power by causing light propagated through a light guide to be incident on a solar cell element provided at a portion of the light guide.

In this photovoltaic power generation device, a portion of sunlight incident from one principal surface of the light guide is caused to propagate through the light guide to be directed to the solar cell element. The light guide contains phosphors (fluorescent substances). The phosphor absorbs sunlight incident on the light guide and thus is excited and emits light (fluorescent light) emitted from the phosphor at this time propagates through the light guide, and is incident on the solar cell element, and thereby electrical power is generated.

In such a photovoltaic power generation device, light emitting ability of the phosphor is included as a factor of determining power production. Thus, in order to increase the power production of the photovoltaic power generation device, it is desired to use a phosphor that enables absorbing of light having a sufficiently long wavelength and has high fluorescence quantum yield. Accordingly, selection of a phosphor is important.

Here, an explanation was made as to a photovoltaic power generation device. However, similarly in other uses such as a fluorescent probe in a living body, it is very important to enable selection of a phosphor having ability of absorbing light with a sufficiently long wavelength.

As a phosphor, various substances are searched for until now. For example, a compound represented by the following expression (9)-1 (abbreviated to a "compound (9)-1") is disclosed in NPL 1 and a compound represented by the following expression (9)-2 (abbreviated to a "compound (9)-2") is disclosed in NPL 2.

[Chem. 1]

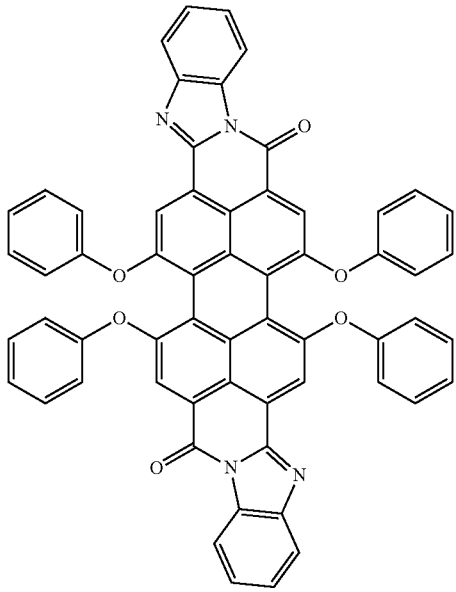

(9)-1

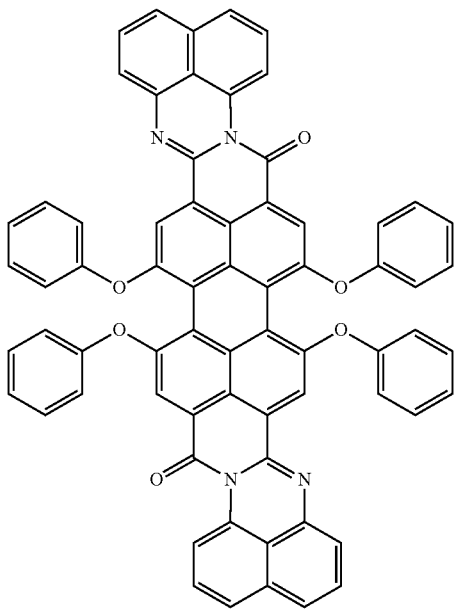

(9)-2

CITATION LIST

Patent Literature

PTL 1: Japanese Unexamined Patent Application Publication No. 3-273686

Non Patent Literature

NPL 1: Michael G. Debije, et al., Appl. Opt., 50(2011)163
NPL 2: Heribert Quante, et al., Chem. Mater., 1997, 9, 495

SUMMARY OF INVENTION

Technical Problem

However, the compound (9)-1 has high fluorescence quantum yield, but a peak wavelength of absorbable light (light absorption peak wavelength) is substantially 630 nm. Thus, the compound (9)-1 has a problem that the absorption wavelength of light is not sufficiently long wavelength. In the compound (9)-2, a light absorption peak wavelength is 650 nm and this is sufficiently long wavelength. However, the compound (9)-2 has a problem that the fluorescence quantum yield is low. As described above, when a compound in which either of the absorption peak wavelength and the fluorescence quantum yield is not sufficient is used in a desired target such as a solar cell module for a photovoltaic power generation device, it is difficult to expect more performance improvement, and thus it is desired to apply a novel compound.

To consider these circumstances, an object of the present invention is to provide a novel compound that enables absorbing of light having sufficiently long wavelength and has high fluorescence quantum yield, a solar cell module using the compound, and a photovoltaic power generation device including the solar cell module.

Solution to Problem

The present invention provides a compound represented by the following general formula (IA) or (IB).

[Chem. 2]

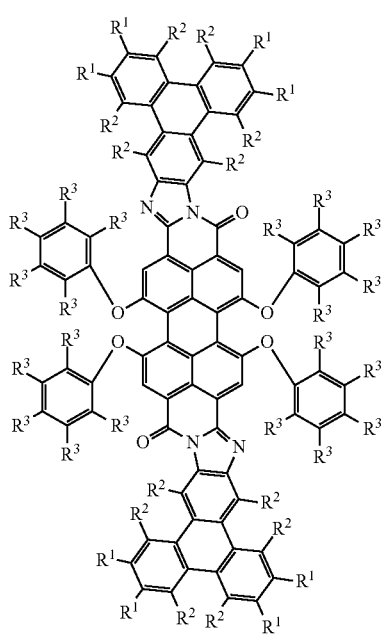

(IA)

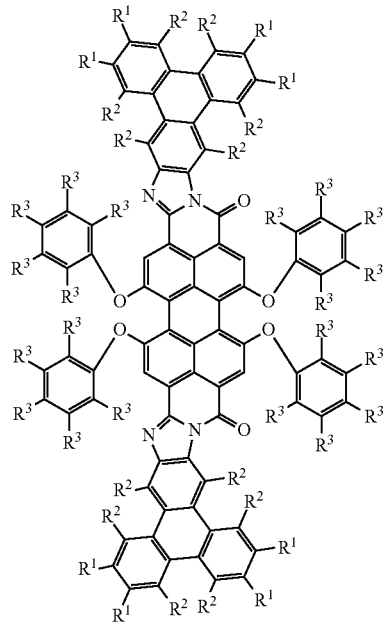

(IB)

(in the formula, $R^1$ and $R^2$ are each independently a hydrogen atom, an alkyl group, an alkoxy group, an aryl group, or an aryloxy group, and a plurality of the $R^1$ and the $R^2$ may be the same as each other or different from each other; $R^3$ corresponds to a hydrogen atom or an alkyl group, and a plurality of $R^3$ may be the same as each other or different from each other)

The invention provides the compound in which the $R^1$ and the $R^2$ are each independently a hydrogen atom, a 10 to 22C alkyl group, a 10 to 22C alkoxy group, a 6C to 22C aryl group, or a 6C to 22C aryloxy group, and the $R^3$ is a hydrogen atom, or a 10 to 22C alkyl group.

The invention provides the compound in which the $R^1$ and the $R^2$ are each independently a hydrogen atom, a 10 to 18C alkyl group, a 10 to 18C alkoxy group, a 6C to 100 aryl group, or a 6C to 100 aryloxy group, and the $R^3$ is a hydrogen atom, or a 6C to 18C alkyl group.

The invention provides the compound in which all of the $R^1$ are groups other than a hydrogen atom.

The invention provides a solar cell module which uses the compound.

The invention provides the solar cell module including a light guide that has a light incident surface and a light exit surface having an area smaller than the light incident surface; and a solar cell element that receives exiting light from the light exit surface so as to generate electrical power, in which the light guide contains the compound, and uses emission light from the compound, which is resulted from absorption of incident light from the light incident surface by the compound, as the exiting light.

The invention provides a photovoltaic power generation device including the solar cell module.

Advantageous Effects of Invention

According to the present invention, there are provided a novel compound that enables absorbing of light having sufficiently long wavelength and has high fluorescence quantum yield, a solar cell module using the compound, and a photovoltaic power generation device including the solar cell module.

BRIEF DESCRIPTION OF DRAWINGS

FIG. 6 is a schematic configuration diagram of a photovoltaic power generation device according to an embodiment of the present invention.

DESCRIPTION OF EMBODIMENTS

Compound

Figure 1:
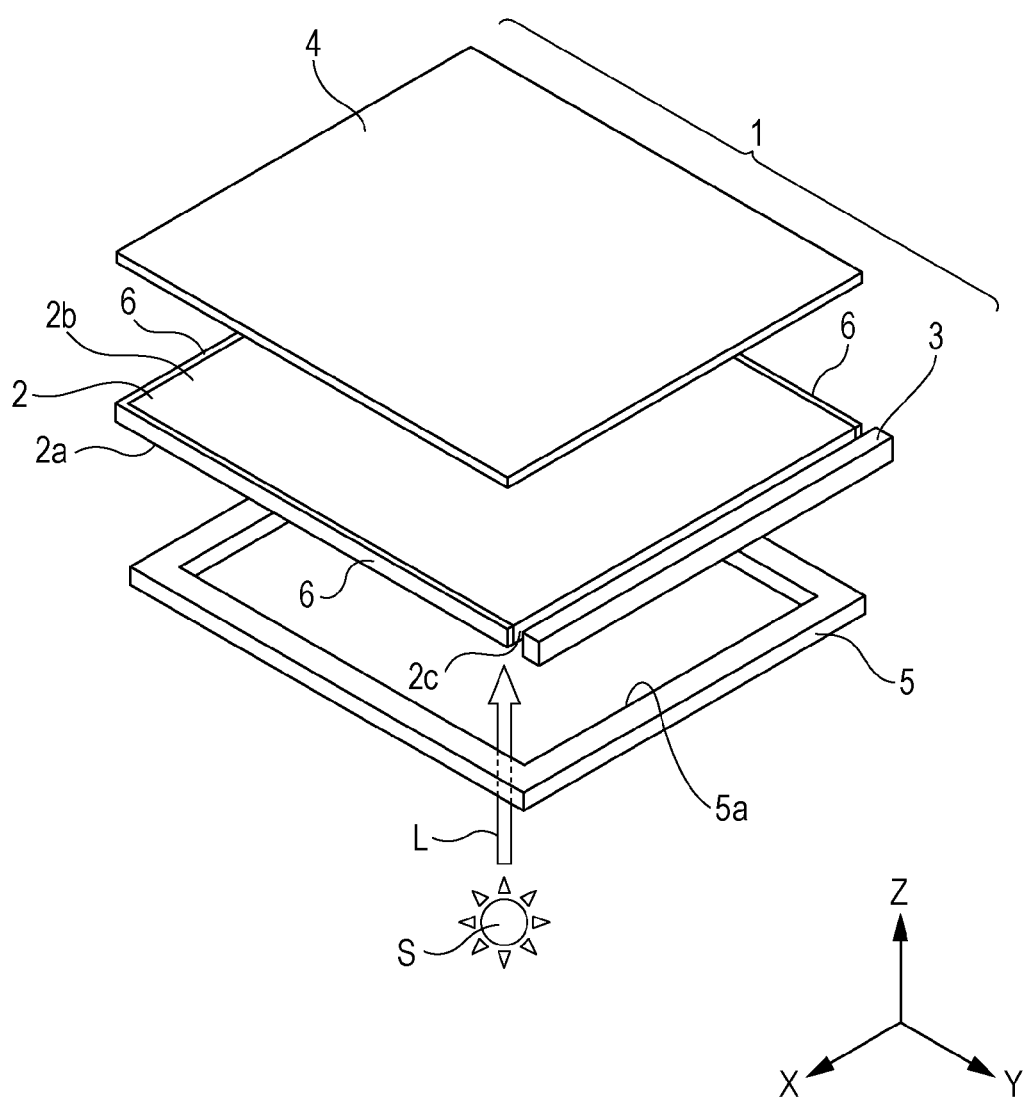
FIG. 1 is a schematic diagram illustrating an overall configuration of a solar cell module according to an embodiment of the present invention.

A compound according to the present invention is represented by the following general formula (IA) or (IB) (these compounds are collectively abbreviated to a compound (I) below). The compound (I) is a novel fluorescent compound and has a high absorption coefficient for long wavelength light, and thus can sufficiently absorb such light. The compound (I) has high fluorescence quantum yield. Among the compounds (I), a compound represented by the following general formula (IA) is set as a syn-object, and a compound represented by the following general formula (IB) is set as an anti-object.

[Chem. 3]

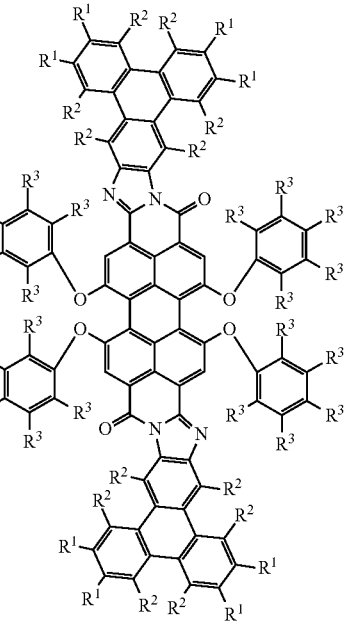

(IA)

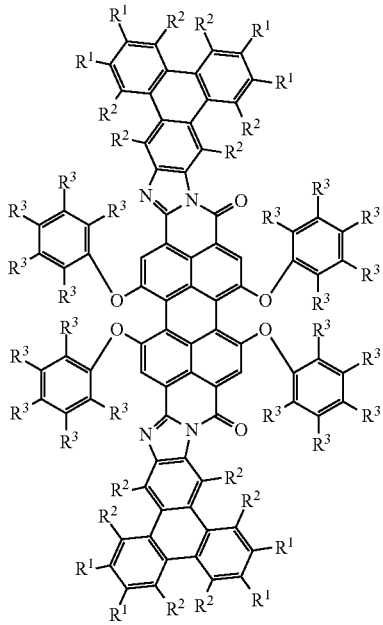

(IB)

(in the formula, the $R^1$ and the $R^2$ are each independently a hydrogen atom, an alkyl group, an alkoxy group, an aryl group, or an aryloxy group, and a plurality of the $R^1$ and the $R^2$ may be the same as each other or different from each other; $R^3$ corresponds to a hydrogen atom or an alkyl group, and a plurality of $R^3$ may be the same as each other or different from each other.)

In the formula, the $R^1$ and the $R^2$ are each independently a hydrogen atom, an alkyl group, an alkoxy group, an aryl group, or an aryloxy group.

In the $R^1$ and the $R^2$, the alkyl group may be any one of a straight chain shape, a branched chain shape, and a cyclic shape. When the alkyl group is cyclic, the alkyl group may be either of a single cyclic shape and a polycyclic shape. In the alkyl group, the number of carbon atoms is preferably in a range of 1 to 22, and more preferably in a range of 1 to 18. The number of carbon atoms is further preferably in a range of 6 to 18 in order to obtain the compound (I) having higher solubility in a solvent which will be described later.

In the alkyl group which has a straight chain shape or a branched chain shape, the number of carbon atoms is preferably in a range of 1 to 22. Examples of the alkyl group may include a methyl group, an ethyl group, an n-propyl group, an isopropyl group, an n-butyl group, an isobutyl group, a sec-butyl group, a tert-butyl group, an n-pentyl group, an isopentyl group, a neopentyl group, a tert-pentyl group, an 1-methylbutyl group, an n-hexyl group, a 2-methylpentyl group, a 3-methylpentyl group, a 2,2-dimethylbutyl group, a 2,3-dimethylbutyl group, an n-heptyl group, a 2-methylhexyl group, a 3-methylhexyl group, a 2,2-dimethylpentyl group, a 2,3-dimethylpentyl group, a 2,4-dimethylpentyl group, a 3,3-dimethylpentyl group, a 3-ethylpentyl group, a 2,2,3-trimethyl-butyl group, an n-octyl group, an isooctyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a heneicosyl group, and a docosyl group.

Among these substances, in the alkyl group which has a straight chain shape or a branched chain shape, the number of carbon atoms is more preferably in a range of 1 to 18. From a view of the solubility of the compound (I), the number of carbon atoms is further preferably in a range of 6 to 18.

In the cyclic alkyl group, the number of carbon atoms is preferably in a range of 3 to 22. Examples of the cyclic alkyl group may include a cyclopropyl group, a cyclobutyl group, a cyclopentyl group, a cyclohexyl group, a cycloheptyl group, a cyclooctyl group, a cyclononyl group, a cyclodecyl group, a norbornyl group, an isobornyl group, a 1-adamantyl group, a 2-adamantyl group, and a tricyclodecyl group. One hydrogen atom or more in the cyclic alkyl group may be substituted with the alkyl group which has a straight chain shape, a branched chain shape, or a cyclic shape. Here, examples of the straight chain alkyl group, the branched chain alkyl group, and the cyclic alkyl group, in which the hydrogen atom is substituted, include the above substances which are described as the alkyl group in the $R^1$ and the $R^2$.

Among these substances, in the cyclic alkyl group, the number of carbon atoms is more preferably in a range of 3 to 18. From a view of the solubility of the compound (I), the number of carbon atoms is further preferably in a range of 6 to 18.

A plurality (eight) of the $R^1$ may be the same as each other or different from each other. That is, all of the $R^1$ may be the same or may be different. In addition, only some of the $R^1$ may be different.

Similarly, a plurality (twelve) of $R^2$ may be the same as each other or different from each other. That is, all of the $R^2$ may be the same or may be different. In addition, only some of the $R^2$ may be different.

Examples of the alkoxy group in the $R^1$ and the $R^2$ may include a univalent group obtained by combining the alkyl group in the $R^1$ and the $R^2$ with an oxygen atom. The number of carbon atoms is preferably in a range of 1 to 22, and more preferably in a range of 1 to 18. From a view of the solubility of the compound (I), the number of carbon atoms is further preferably in a range of 6 to 18.

The aryl group in the $R^1$ and the $R^2$ may be either of a single cyclic shape and a polycyclic shape. In the aryl group, the number of carbon atoms is preferably in a range of 6 to 22. Examples of the aryl group may include a phenyl group, a 1-naphthyl group, a 2-naphthyl group, an o-tolyl group, an m-tolyl group, a p-tolyl group, a xylyl group (dimethyl phenyl group), and the like. One hydrogen atom or more in the aryl group may be substituted with these aryl groups or the alkyl group in the $R^1$ and the $R^2$. In the aryl group having substituents, the number of carbon atoms including the substituents is preferably in a range of 6 to 22.

Among these substances, in the aryl group, the number of carbon atoms is preferably in a range of 6 to 10.

Examples of the aryloxy group in the $R^1$ and the $R^2$ may include a univalent group obtained by combining the aryl group in the $R^1$ and the $R^2$ with an oxygen atom. In the aryloxy group, the number of carbon atoms is preferably in a range of 6 to 22, and more preferably in a range of 6 to 10.

When either of one or more of the $R^1$ or the $R^2$ is the alkyl group, the alkoxy group, the aryl group, or the aryloxy group, the position or the number of these groups in the compound (I) is not particularly limited.

It is preferable that the $R^1$ and the $R^2$ are each independently a hydrogen atom, a 10 to 22C alkyl group or a 1C to 22C alkoxy group, a 6C to 22C aryl group, or a 6C to 22C aryloxy group. It is more preferable that the $R^1$ and the $R^2$ are each independently a hydrogen atom, a 1C to 18C alkyl group or a 10 to 18C alkoxy group, a 6C to 100 aryl group, or a 6C to 100 aryloxy group.

When a molecule has one or more alkyl group as the $R^1$ or the $R^2$, the compound (I) has improved solubility for a solvent as described above by selecting an appropriate solvent. Handling properties of the compound (I) is more improved by using the compound (I) which has high solubility for a solvent, and thus a target is more easily obtained. For example, more power production in a photovoltaic power generation device (which will be described later) is obtained, or higher detection sensitivity in a fluorescent probe is obtained. Even though the compound (I) which has none of the alkyl groups is used as the $R^1$ and $R^2$, a sufficiently useful target is obtained.

In the formula, the $R^3$ corresponds to a hydrogen atom or an alkyl group.

Examples of the alkyl group in the $R^3$ may include similar substances with the alkyl group in the $R^1$ and the $R^2$. The alkyl group in the $R^3$ may be the same as or different from the alkyl group in the $R^1$ and the $R^2$ in the same molecule.

A plurality (20) of the $R^3$ may be the same as each other or different from each other. That is, all of the $R^3$ may be the same or may be different. In addition, only some of the $R^3$ may be different.

When either of one or more of the $R^3$ is the alkyl group, the position or the number of the alkyl group in the compound (I) is not particularly limited. Among these substances, it is preferable that the $R^3$ (at a paraposition for an oxygen atom) which is combined to a 4-position carbon atom is the alkyl group in a benzene ring skeleton in which the $R^3$ and the oxygen atom are combined. The number of skeletons in which the $R^3$ combined to the 4-position carbon atom is the alkyl group is preferably two or more among four benzene ring skeletons, and three or more is more preferable. It is particularly preferable that the $R^1$ combined to the 4-position carbon atom in all the four benzene ring skeletons is the alkyl group.

Since the four benzene ring skeletons to which the $R^3$ is combined in the compound (I) has relatively large steric hindrance, rotation using combination between adjacent oxygen atoms as an axis is difficult. For example, regarding 2 molecules of the compound (I), a case where the benzene ring skeletons are not rotated is considered with a focus on benzene ring skeletons at the same position. In one compound (I), the alkyl group is combined as the $R^3$ to a 2-position carbon atom of the benzene ring skeleton and hydrogen atoms are combined as the $R^3$ to all of other carbon atoms. By the way, in another compound (I), the alkyl group is combined as the $R^3$ to a 6-position carbon atom of the benzene ring skeleton and hydrogen atoms are combined as the $R^3$ to all of other carbon atoms. In these compounds (I), for example, even though the alkyl groups are the same, the alkyl groups may be distinguished as a stereoisomer. Similarly, even though the alkyl groups are the same, the alkyl groups may be distinguished as a stereoisomer in the compound (I) in which the alkyl group is combined as the $R^3$ to a 3-position carbon atom of the benzene ring skeleton and hydrogen atoms are combined as the $R^3$ to all of other carbon atoms, and the compound (I) in which the alkyl group is combined as the $R^3$ to a 5-position carbon atom of the benzene ring skeleton and hydrogen atoms are combined as the $R^3$ to all of other carbon atoms.

The above-described substances are described as only an example, and the stereoisomer is not limited to above-described substances.

It is preferable that the $R^3$ is a hydrogen atom or a 1C to 22C alkyl group, and it is more preferable that the $R^3$ is a hydrogen atom or a 6C to 18C alkyl group. If the number of carbon atoms in the alkyl group is equal to or greater than 6, the compound (I) may have improved solubility for a solvent.

The compound (I) has two triphenylene skeletons to which the $R^1$ and the $R^2$ are combined, and thereby a light absorption peak wavelength becomes a long wavelength. Thus, the fluorescence quantum yield increases.

In this specification, the "peak wavelength" means a wavelength at a main peak in an optical spectrum and preferably means a wavelength at a peak having the maximum spectral intensity.

In the compound (I), the two triphenylene skeletons are preferably the same as each other, from a view of easy manufacturing obtained by using a manufacturing method (which will be described later).

The compound (I) has the light absorption peak wavelength which is preferably equal to or greater than 650 nm and the light absorption wavelength is a sufficiently long wavelength.

The light absorption peak wavelength of the compound (I) and a peak wavelength of the emitted light may be obtained by quantum chemical calculation. At this time, general quantum chemical calculation software may be used, and Gaussian09 (manufactured by Gaussian Corporation) may be included as such the software. For example, the light absorption peak wavelength may be obtained by using a calculation condition set to be B3LYP/6-31+g(d). The calculation condition is not limited thereto.

A substance in which one or more $R^1$ is a group (alkyl group, alkoxy group, aryl group, or aryloxy group) other than the hydrogen atom may be included as a preferable compound (I). It is preferable that two or more $R^1$ are groups other than the hydrogen atom. It is more preferable that four or more $R^1$ are groups other than the hydrogen atom. As such a compound (I), a substance in which all (eight) $R^1$ are groups other than the hydrogen atom may be used, but it is not limited thereto.

The compound (I) can sufficiently absorb light of a long wavelength and the peak wavelength of emitted light is a sufficiently long wavelength. The compound (I) has the high fluorescence quantum yield. Accordingly, for example, a photovoltaic power generation device (which will be described later) has excellent power production by using the compound (I) as a phosphor in the photovoltaic power generation device. A fluorescent probe has higher detection sensitivity by using the compound (I) for the fluorescent probe. The purpose of using the compound (I) is not limited thereto, and the compound (I) may be used in all fields of using a phosphor.

The compound (I) may be manufactured by a manufacturing method. For example, the manufacturing method includes a process (below abbreviated to a "compound (Ib) manufacturing process) and a process (below abbreviated to a "compound (I) manufacturing process"). In the compound (Ib) manufacturing process, a compound (below abbreviated to a "compound (Id)") represented by the following general formula (Id) is caused to react with a compound (below abbreviated to a "compound (Ic)") represented by the following general formula (Ic) and thereby a compound (below abbreviated to a "compound (Ib)") represented by the following general formula (Ib) is obtained. In the compound (I) manufacturing process, the compound (Ib) is caused to react with a compound (below abbreviated to a "compound (Ia)") represented by the following general formula (Ia). The manufacturing method described herein is only an example, and the manufacturing method of the compound (I) is not limited thereto.

The following reaction formula shows an example in which a compound represented by the general formulas (IA) and (IB) is also generated as the compound (I). However, only one of the compounds may be generated in accordance with a reaction condition.

[Chem. 4]

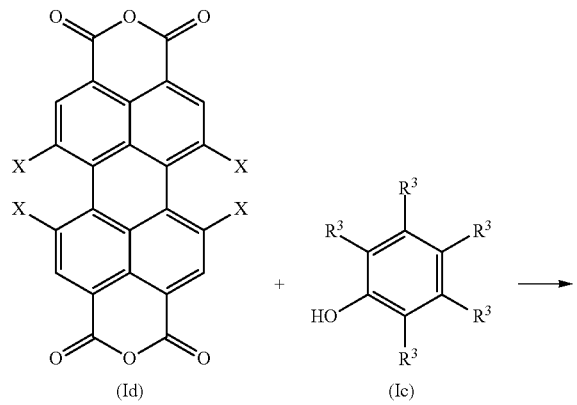

(Id)      (Ic)

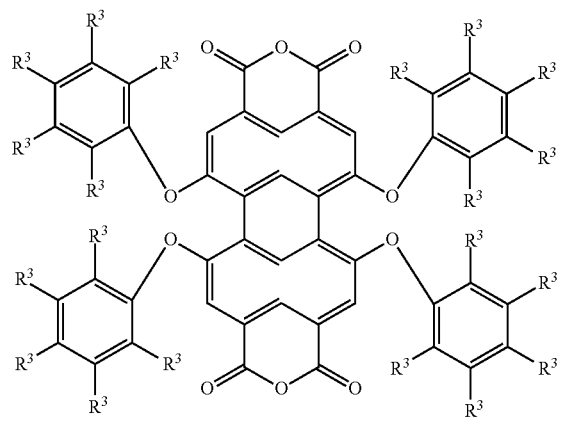
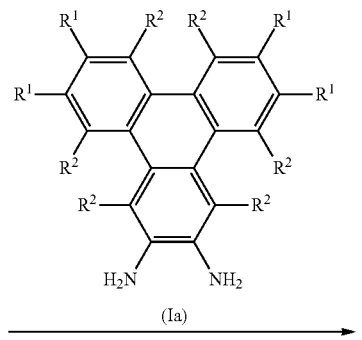

(Ib)                                   (Ia)

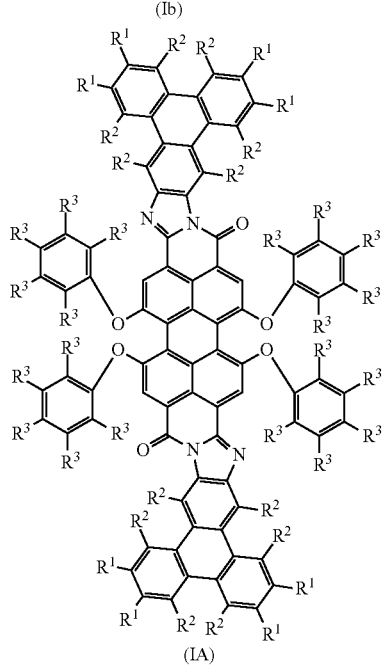
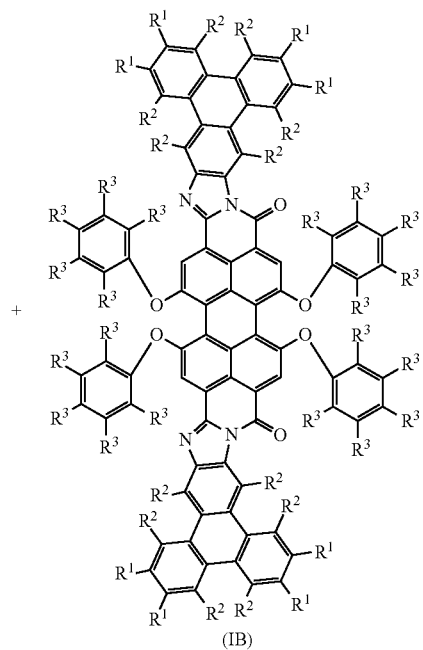

(IA)                                    (IB)

(In the formula, the $R^1$, the $R^2$, and the $R^3$ are the same as those described above; X is a halogen atom.)

In the compound (Ib) manufacturing process, the compounds (Ic) and (Id) are caused to react with each other.

In the compound (Ic), the $R^3$ is the same as the $R^3$ in the general formulas (IA) and (IB).

In the compound (Id), X is a halogen atom, and preferably is a chlorine atom, a bromine atom, or an iodine atom. A plurality (four) of X may be the same as each other or different from each other, but it is preferable that all X are the same.

In the compound (Ib) manufacturing process, it is preferable that a reaction is performed by using a solvent. The solvent may be appropriately selected from substances that do not disturb a reaction, considering solubility of a compound being a raw material, a reaction condition, or the like. Examples of a specific solvent include an amide compound such as N-methylpyrrolidone, N,N-dimethylformamide, and N,N-dimethylacetamide, and the like.

In the compound (Ib) manufacturing process, a reaction is preferably performed by using a base such as potassium carbonate and sodium carbonate.

In the compound (Ib) manufacturing process, a usage of the compound (Ic) is preferably equal to or greater than 4 mole times the compound (Id), and is more preferably 4 to 8 mole times the compound (Id). The usage of the base is preferably equal to or greater than 1 mole time the compound (Ic), and is more preferably 1 to 6 mole times the compound (Ic).

In the compound (Ib) manufacturing process, a reaction temperature of the reaction is preferably in a range of 50° C. to 180° C., and a reaction period of time is preferably in a range of 6 hours to 72 hours.

In the compound (Ib) manufacturing process, after the reaction is completed, post-treatment is performed as necessary by using a well-known method, and then the compound (Ib) may be taken out. That is, any one of post-treatment operations such as filtration, washing, extraction, pH adjustment, dehydration, and concentration may be independently performed, or combination of two or more operations may be performed, and thus the compound (Ib) may be taken out by using concentration, crystallization, reprecipitation, column chromatography, or the like. The taken compound (Ib) may be refined as necessary in such a manner that one of operations of crystallization, reprecipitation, column chromatography, extraction, stirred washing of a crystal with a solvent, and the like is independently performed once or more, or combination of two or more operations is performed once or more.

In the compound (Ib) manufacturing process, after the reaction is completed, and then post-treatment is performed as necessary, subsequently the compound (I) manufacturing process may be performed without taking out of the compound (Ib).

In the compound (I) manufacturing process, the compounds (Ia) and (Ib) are caused to react with each other. The reaction is a dehydrative condensation reaction.

In the compound (Ia), the $R^1$ and the $R^2$ are the same as the $R^1$ and the $R^2$ in the general formulas (IA) and (IB).

In the compound (I) manufacturing process, it is preferable that the reaction is performed by using a solvent. The solvent may be appropriately selected from substances that do not disturb a reaction, considering solubility of a compound being a raw material, a reaction condition, or the like. Examples of a specific solvent include an aromatic compound such as toluene and phenol.

In the compound (I) manufacturing process, it is preferable that the reaction is performed by using a base such as pyridine and pyrazine.

In the compound (I) manufacturing process, a usage of the compound (Ia) is preferably equal to or greater than 2 mole times the compound (Ib), and is more preferably 4 to 5 mole times the compound (Ib). A usage of the base is preferably equal to or greater than 1 mole time the compound (Ia), and is more preferably 1 to 4 mole times the compound (Ia).

In the compound (I) manufacturing process, a reaction temperature is preferably in a range of 50° C. to 180° C., and a reaction period of time is preferably in a range of 6 hours to 72 hours.

The reaction may be performed with removing of water produced as a byproduct by azeotropic dehydration, for example. At this time, an appropriate amount of the solvent may be added during the reaction.

In the compound (I) manufacturing process, when one type of compound is used as the compounds (Ia) and (Ib), two types of compounds (I) represented by the general formulas (IA) and (IB) may be also produced. When multiple types of compounds are used for at least one of the compounds (Ia) and (Ib), multiple types of the compounds (I) may be produced. In this manner, when the multiple types of the compounds (I) are produced and some types of the compounds (I) are used among the produced multiple types of the compounds (I), targets may be separated by using a similar method to in a case of the compound (Ib), or a generation rate of a target may be improved by controlling the reaction condition.

In the compound (I) manufacturing process, after the reaction is completed, the compound (I) may be taken out or the taken compound (I) may be refined by using a similar method to in a case of the compound (Ib) manufacturing process.

In the above-described manufacturing method, when it is impossible to acquire a commercial product of the compound (Ia), the compound (Ia) may be manufactured by using a method which is obtained by combining well-known methods and is described as follows.

That is, the compound (Ia) may be manufactured by using a manufacturing method. For example, the manufacturing method includes a process (below abbreviated to a "compound (Iab) manufacturing process"), a process (below abbreviated to a "compound (Iaa) manufacturing process"), and a process (below abbreviated to a "compound (Ia) manufacturing process"). In the compound (Iab) manufacturing process, a compound (below abbreviated to a "compound (Iad)") represented by the following general formula (Iad) is caused to react with a compound (below abbreviated to a "compound (Iac)") represented by the following general formula (Iac), and thereby a compound (below abbreviated to a "compound (Iab)") represented by the following general formula (Iab) is obtained. In the compound (Iaa) manufacturing process, the compound (Iab) is caused to react and thereby a compound (below abbreviated to a "compound (Iaa)") represented by the following general formula (Iaa) is obtained. In the compound (Ia) manufacturing process, the compound (Iaa) is caused to react and thereby the compound (Ia) is obtained. The manufacturing method described herein is only an example, and the manufacturing method of the compound (Ia) is not limited thereto.

[Chem. 5]

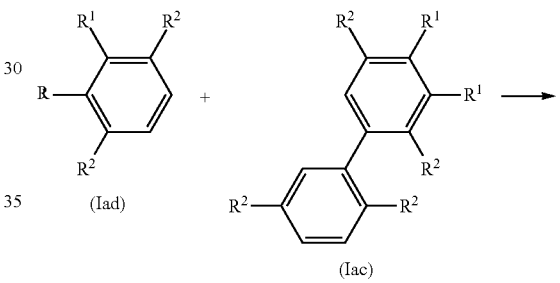

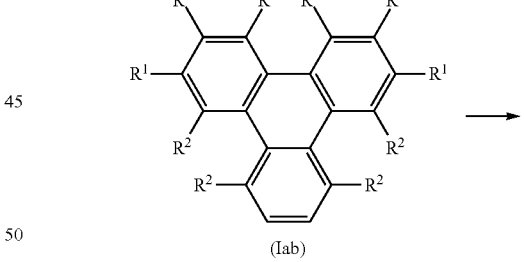

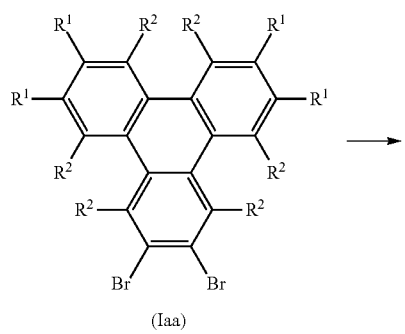

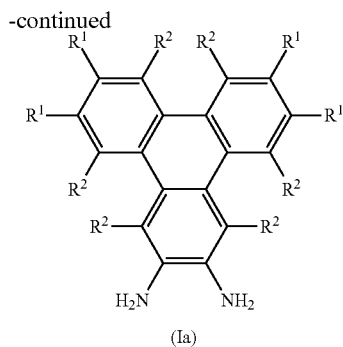

(Ia)

(In the formula, the $R^1$ and the $R^2$ are the same as those described above.

In the compound (Iab) manufacturing process, the compounds (Iac) and (Iad) are caused to react with each other.

In the compound (Iac) and the compound (Iad), the $R^1$ and the $R^2$ are the same as the $R^1$ and the $R^2$ in the general formulas (IA) and (IB).

In the compound (Iab) manufacturing process, it is preferable that the reaction is performed by using a solvent. The solvent may be appropriately selected from substances that do not disturb a reaction, considering solubility of a compound being a raw material, a reaction condition, or the like. Examples of a specific solvent include halogenated hydrocarbon such as dichloromethane, and the like.

In the compound (Iab) manufacturing process, it is preferable that the reaction is performed by using iron (III) chloride.

In the compound (Iab) manufacturing process, a usage of the compound (Iad) is preferably equal to or greater than 1 mole time the compound (Iac), and is more preferably 1 to 6 mole times the compound (Iac).

A usage of the iron (III) chloride is preferably equal to or greater than 2 mole times the compound (Iac), and is more preferably 2 to 12 mole times the compound (Iac).

In the compound (Iab) manufacturing process, a reaction temperature of the reaction is preferably in a range of 5° C. to 40° C., and a reaction period of time is preferably in a range of 0.5 hours to 10 hours.

In the compound (Iab) manufacturing process, after the reaction is completed, the compound (Iab) may be taken out or the taken compound (Iab) may be refined by using a similar method to in a case of the compound (Ib) manufacturing process. After the reaction is completed, and then post-treatment is performed as necessary, subsequently the next manufacturing process may be performed without taking out of the compound (Iab).

In the compound (Iaa) manufacturing process, the compound (Iaa) is obtained from the compound (Iab). In order to obtain the compound (Iaa), for example, the reaction is performed under a condition, that is, at a temperature of preferably −10° C. to 5° C., and for preferably 0.5 hours to 10 hours by using halogenated hydrocarbon such as dichloromethane as a reaction solvent, and using bromine ($Br_2$).

In the compound (Iaa) manufacturing process, a usage of the bromine is preferably equal to or greater than 2 mole times the compound (Iab), and is more preferably 2 to 8 mole times the compound (Iab).

In the compound (Iaa) manufacturing process, after the reaction is completed, the compound (Iaa) may be taken out or the taken compound (Iaa) may be refined by using a similar method to in a case of the compound (Ib) manufacturing process. After the reaction is completed, and then post-treatment is performed as necessary, subsequently the next manufacturing process may be performed without taking out of the compound (Iaa).

In the compound (Ia) manufacturing process, the compound (Ia) is obtained from the compound (Iaa). In order to obtain the compound (Ia), an amination reaction may be performed. For example, a method disclosed in "J. Am. Chem. Soc., 2009, 131, 7287" may be used. That is, at first, a reaction on the compound (Iaa) is performed at an inert gas atmosphere such as an argon gas, by using aromatic hydrocarbon such as toluene, as a reaction solvent and by using a base (strong base) such as sodium tert-butoxide and potassium tert-butoxide, benzophenone imine ($HN=C(C_6H_5)_2$), a palladium catalyst such as tris (dibenzylidene acetone) dipalladium (0) ($Pd_2(dba)_3$), and an asymmetric ligand such as (±)-2,2'-bis(diphenylphosphino)-1,1'-binaphthyl. Thus, two bromine atoms (—Br) are substituted with a group represented by a formula of "—$N=C(C_6H_5)_2$". A usage of each of the base and the benzophenone imine is preferably equal to or greater than 2 mole times the compound (Iaa), and is more preferably 2 to 4 mole times the compound (Iaa). A usage of each of the palladium catalyst and the asymmetric ligand is preferably 0.002 to 0.2 mole times the compound (Iaa). The reaction is preferably performed under a heating and reflux condition, and is preferably performed under a condition, that is, for 2 hours to 20 hours.

An acid treatment is performed on the obtained intermediate by using an ether compound such as tetrahydrofuran, as a reaction solvent, and by using acid such as hydrochloric acid. Thus, two groups represented by a formula of "—$N=C(C_6H_5)_2$" are substituted with an amino group (—$NH_2$). A usage of the acid is preferably equal to or greater than 2 mole times the intermediate, and is more preferably 2 to 4 mole times the intermediate.

In the compound (Ia) manufacturing process, after the reaction is completed, the intermediate or the compound (Ia) may be taken out or the taken intermediate or compound (Ia) may be refined by using a similar method to in a case of the compound (Ib) manufacturing process. Additionally, after the reaction is completed, and then post-treatment is performed as necessary, subsequently the next manufacturing process may be performed without taking out of the intermediate or the compound (Ia).

In the above-described method, it may be impossible to acquire a commercial product which is used as the compound (Iac) or the compound (Iad), and has the desired $R^1$ or $R^2$, in accordance with a type of the compound (Iab) which will be used. In this case, instead of the compound (Iac) or the compound (Iad) which is to be used, the compound (Iab) may be manufactured by using a different compound as a raw material, and using a manufacturing method which includes a process of converting a group other than a target to the desired $R^1$ or $R^2$. Here, the different compound refers to a compound having a group other than the target, for example, a compound having a group of $R^1$ or $R^2$ which is different from the desired $R^1$ or $R^2$, or a compound having the $R^1$ or $R^2$ which is substituted with the other group.

When it is impossible to acquire the compounds (Iac) and (Iad) which have the desired $R^1$, a method of manufacturing the compound (Iab) will be described below.

That is, the compound (Iab) may be manufactured by using a manufacturing method. For example, the manufacturing method includes a process (below abbreviated to a "compound (Iabb) manufacturing process"), a process (below abbreviated to a "compound (Iaba) manufacturing process"), and a process (below abbreviated to a "compound (Iab) manufacturing process (2)"). In the compound (Iabb) manufacturing process, a compound (below abbreviated to a "compound (Iabd)") represented by the following general formula (Iabd) is caused to react with a compound (below abbreviated to a "compound (Iabc)") represented by the following general formula (Iabc), and thereby a compound (below abbreviated to a "compound (Iabb)") represented by the following general formula (Iabb) is obtained. In the compound (Iaba) manufacturing process, the compound (Iabb) is caused to react and thereby a compound (below abbreviated to a "compound (Iaba)") represented by the following general formula (Iaba) is obtained. In the compound (Iab) manufacturing process (2), the compound (Iaba) is caused to react and thereby the compound (Iab) is obtained. Here, the compound (Iabd) is one type of the compound (Iad) and the compound (Iabc) is one type of the compound (Iac). The manufacturing method described herein is only an example, and the manufacturing method of the compound (Iab) is not limited thereto.

[Chem. 6]

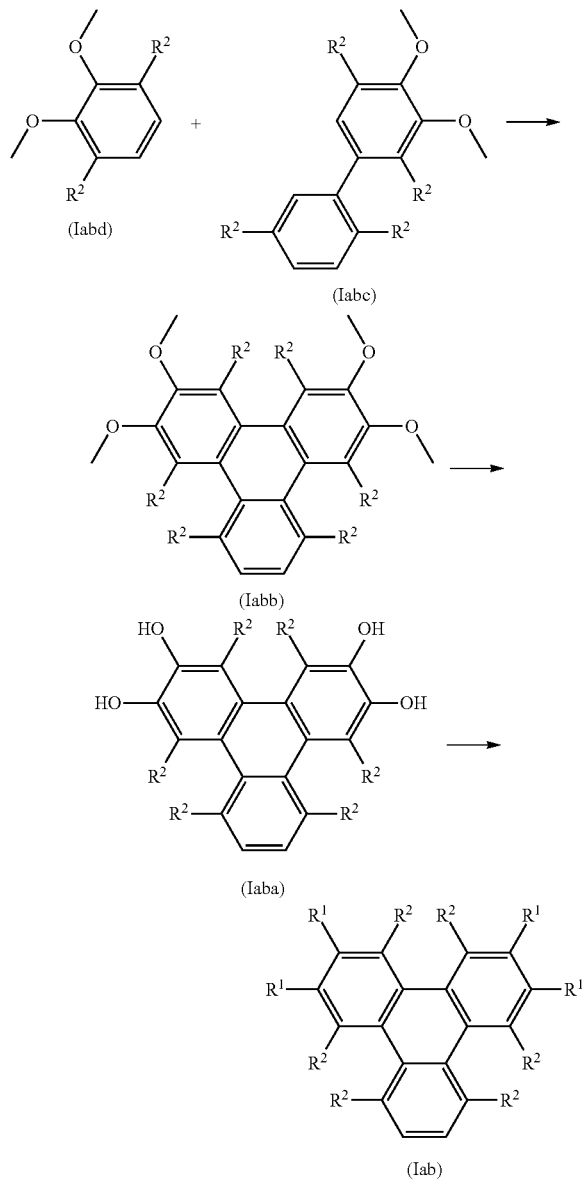

(In the formula, the $R^1$ and the $R^2$ are the same as those described above.)

In the compound (Iabb) manufacturing process, the compounds (Iabc) and (Iabd) are caused to react with each other. The compound (Iabb) manufacturing process may be performed by using a similar method to the compound (Iab) manufacturing process, in addition to using of the compounds (Iabc) and (Iabd) instead of the compounds (Iac) and (Iad).

In the compound (Iaba) manufacturing process, the compound (Iaba) is obtained from the compound (Iabb). In order to obtain the compound (Iaba), for example, the reaction is performed by using organic acid such as acetic acid, as a reaction solvent, and using hydrogen bromide (HBr) and the reaction is performed preferably under a heating and reflux condition, and is performed preferably under a condition, that is, for 2 hours to 20 hours.

In the compound (Iaba) manufacturing process, it is preferable that a usage of the hydrogen bromide is much more excessive than that of the compound (Iabb), and for example, the usage of the hydrogen bromide is preferably 10 to 100 mole times the compound (Iabb).

In the compound (Iaba) manufacturing process, after the reaction is completed, the compound (Iaba) may be taken out or the taken compound (Iaba) may be refined by using a similar method to in a case of the compound (Ib) manufacturing process. Additionally, after the reaction is completed, and then post-treatment is performed as necessary, subsequently the next manufacturing process may be performed without taking out of the compound (Iaba).

In the compound (Iab) manufacturing process (2), the compound (Iab) is obtained from the compound (Iaba). In order to obtain the compound (Iab), for example, the reaction is performed under a condition, that is, at a temperature of preferably 50° C. to 140° C., and for preferably 1 hour to 24 hours, by using amide compound such as N-methylpyrrolidone, N,N-dimethylformamide, and N,N-dimethylacetamide, and the like, as a reaction solvent, and by using a base such as potassium carbonate and sodium carbonate, and bromide represented by a general formula of "$R^1$—Br" (in the formula, the $R^1$ is the same as that described above).

In the compound (Iab) manufacturing process (2), a usage of the bromide is preferably equal to or greater than 4 mole times the compound (Iaba), and is more preferably 4 to 8 mole times the compound (Iaba). A usage of the base is preferably equal to or greater than 1 mole time the bromide, and is more preferably 1 to 3 mole times the bromide.

In the compound (Iab) manufacturing process (2), after the reaction is completed, the compound (Iab) may be taken out or the taken compound (Iab) may be refined by using a similar method to in a case of the compound (Ib) manufacturing process. Additionally, after the reaction is completed, and then post-treatment is performed as necessary, subsequently the next manufacturing process may be performed without taking out of the compound (Iab).

Here, a case in which a methyl ether compound is used as the compounds (Iabc) and (Iabd) is described. However, other ether compound other than the methyl ether may be used.

Here, a case is described in which when it is impossible to acquire a commercial product which is used as the compounds (Iac) and (Iad) and has the desired $R^1$, the compound (Iab) is manufactured by using a different compound which has a group which is used as the $R^1$ and is different from the desired $R^1$ as a raw material, and using a manufacturing method which includes a process of substituting the group with the desired $R^1$. However, when it is impossible to acquire a commercial product which is used as the compounds (Iac) and (Iad) and has the desired $R^2$, and when it is impossible to acquire a commercial product which is used as the compounds (Iac) and (Iad), and has the desired $R^1$ or $R^2$, the compound (Iab) may be manufactured by using the similar method.

A substance obtained by the following manufacturing method in accordance with the well-known method may be used as the compound (Iac) in the above-described manufacturing method.

That is, if Suzuki-Miyaura coupling is used, the compound (Iac) may be manufactured by using a manufacturing method. For example, the manufacturing method includes a process (below abbreviated to a "compound (Iac) manufacturing process"). In the compound (Iac) manufacturing process, a compound (below abbreviated to a "compound (Iaca)") represented by the following general formula (Iaca) is caused to react with a compound (below abbreviated to a "compound (Iacb)") represented by the following general formula (Iacb), and thereby the compound (Iac) is obtained. The manufacturing method described herein is only an example, and the manufacturing method of the compound (Iac) is not limited thereto.

[Chem. 7]

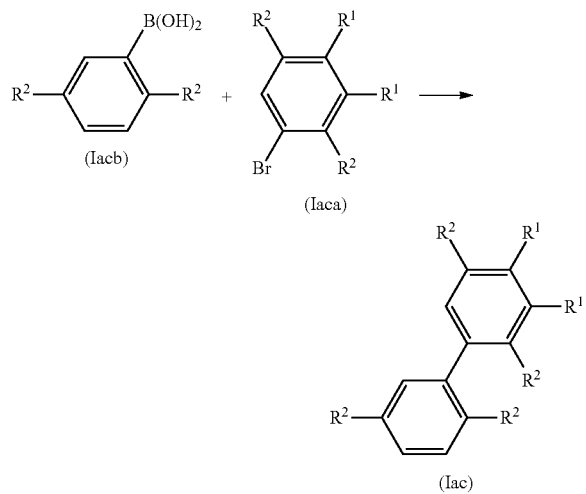

(In the formula, the $R^1$ and the $R^2$ are the same as those described above.)

In the compound (Iac) manufacturing process, the compounds (Iaca) and (Iacb) are caused to react with each other.

In the compounds (Iaca) and (Iacb), the $R^1$ and the $R^2$ are the same as the $R^1$ and the $R^2$ in the general formulas (IA) and (IB).

In the compound (Iac) manufacturing process, it is preferable that the reaction is performed at an inert gas atmosphere such as an argon gas, by using a solvent mixture of water and aromatic hydrocarbon such as toluene, as a reaction solvent.

In the compound (Iab) manufacturing process, the reaction is preferably performed by using a base such as potassium carbonate and sodium carbonate, and a palladium catalyst such as $PdCl_2(PPh_3)_2$.

In the compound (Iac) manufacturing process, a usage of the compound (Iacb) is preferably equal to or greater than 1 mole time the compound (Iaca), and is more preferably 1 to 3 mole times the compound (Iaca). A usage of the base is preferably 1 to 6 mole times the compound (Iaca), and a usage of the palladium catalyst is preferably 0.005 to 0.05 mole times the compound (Iaca).

In the compound (Iac) manufacturing process, the reaction is preferably performed under a heating and reflux condition, and is preferably performed under a condition, that is, for 2 hours to 20 hours.

In the compound (Iac) manufacturing process, after the reaction is completed, the compound (Iac) may be taken out or the taken compound (Iac) may be refined by using a similar method to in a case of the compound (Ib) manufacturing process. Additionally, after the reaction is completed, and then post-treatment is performed as necessary, subsequently the next manufacturing process may be performed without taking out of the compound (Iac).

A substance obtained by using a process (abbreviated to a "compound (Id) manufacturing process") of obtaining the compound (Id), for example, as follows, in accordance with the well-known method may be used as the compound (Id) in the above-described manufacturing method.

That is, the compound (Id) is obtained by mixing 3,4,9,10-perylene tetracarboxylic acid dianhydride, a chlorization agent such as chlorosulfuric acid, and iodine ($I_2$) and causing these substances to react with each other at an inert gas atmosphere such as an argon gas.

It is preferable that a usage of the chlorization agent is much more excessive than that of the 3,4,9,10-perylene tetracarboxylic acid dianhydride, and for example, the usage of the chlorization agent is preferably 10 to 50 mole times the 3,4,9,10-perylene tetracarboxylic acid dianhydride. A usage of the iodine is preferably 0.02 to 0.8 mole times the 3,4,9, 10-perylene tetracarboxylic acid dianhydride.

The reaction temperature of the reaction is preferably in a range of 40° to 100°, and a reaction period of time is preferably in a range of 0.2 hours to 10 hours.

After the reaction is completed, the compound (Id) may be taken out or the taken compound (Id) may be refined by using a similar method to in a case of the compound (Ib) manufacturing process. Additionally, after the reaction is completed, and then post-treatment is performed as necessary, subsequently the next manufacturing process may be performed without taking out of the compound (Id).

In the above-described manufacturing method, the compound (Ib) may be obtained by using a method as follows. A carboxylic acid anhydride part (—C(=O)—O—C(=O)—) is substituted (protected) with another structure as necessary in the compound (Id), and then this compound and the compound (Ic) are caused to react with each other. Then, in a compound obtained by the reaction, the substitution part is recovered (deprotected) to an original carboxylic acid anhydride part, and thereby the compound (Ib) may be obtained.

An example of such a method of obtaining the compound (Ib) includes a method including a process (below abbreviated to a "compound (Ibb) manufacturing process"), a process (below abbreviated to a "compound (Iba) manufacturing process"), and a process (below abbreviated to a "compound (Ib) manufacturing process (2)"). In the compound (Ibb) manufacturing process, the compound (Id) is caused to react and thereby a compound (below abbreviated to a "compound (Ibb)") represented by the following general formula (Ibb) is obtained. In the compound (Iba) manufacturing process, the compound (Ibb) and the compound (Ic) are caused to react with each other, and thereby a compound (below abbreviated to a "compound (Iba)") represented by the following general formula (Iba) is obtained. In the compound (Ib) manufacturing process (2), the compound (Iba) is caused to react and thereby the compound (Ib) is obtained. However, the method of obtaining the compound (Ib) is not limited thereto.

[Chem. 8]

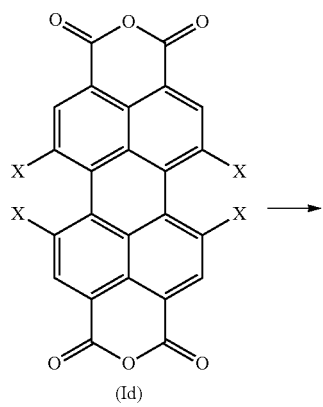
(Id)

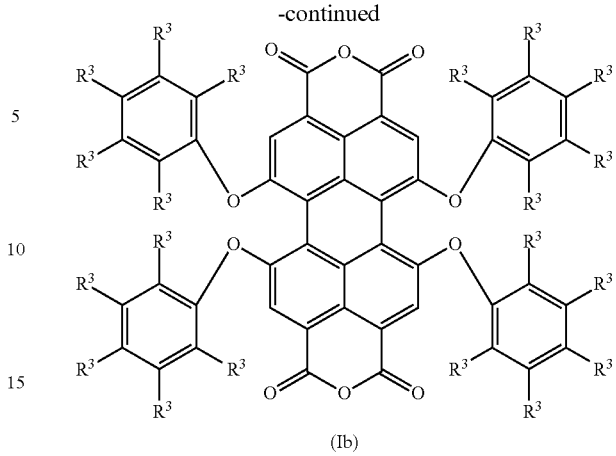
(Ib)

(In the formula, the $R^3$ and the X are the same as those described above; the $R^9$ is an alkyl group.)

In the compound (Ibb) manufacturing process, the compound (Ibb) is obtained from the compound (Id).

In the compound (Ibb), the X is the same as the X in the general formula (Id).

In the compound (Ibb) manufacturing process, for example, the reaction is performed under a condition, that is, at a temperature of preferably 100° C. to 180° C., and for preferably 6 hours to 72 hours, by using organic acid such as propionic acid, as a reaction solvent, and by using an amine compound represented by a general formula of "$R^9$—$NH_2$" (in the formula, the $R^9$ is an alkyl group).

An example of the alkyl group in the $R^9$ includes a similar substance to the alkyl group in the $R^1$ and the $R^2$. The number of carbon atoms is preferably in a range of 3 to 10. The alkyl group has preferably a straight chain shape or a branched chain shape and has more preferably the straight chain shape.

In the compound (Ibb) manufacturing process, a usage of the amine compound is preferably equal to or greater than 2 mole times the compound (Id), and is preferably 2 to 6 mole times the compound (Id).

In the compound (Ibb) manufacturing process, after the reaction is completed, the compound (Ibb) may be taken out or the taken compound (Ibb) may be refined by using a similar method to in a case of the compound (Ib) manufacturing process. Additionally, after the reaction is completed, and then post-treatment is performed as necessary, subsequently the next manufacturing process may be performed without taking out of the compound (Ibb).

In the compound (Iba) manufacturing process, the compounds (Ibb) and (Ic) are caused to react with each other.

The compound (Iba) manufacturing process may be performed by using a similar method to the compound (Tb) manufacturing process, in addition to using of the compound (Ibb) instead of the compound (Id).

In the compound (Ib) manufacturing process (2), the compound (Ib) is obtained from the compound (Iba). In order to obtain the compound (Ib), for example, the reaction is performed preferably under a heating and reflux condition and a condition, that is, for preferably 24 hours to 120 hours, by using alcohol such as ethanol and 2-propanol, as a reaction solvent, and using water, a base such as sodium hydroxide, potassium hydroxide, and the like.

In the compound (Ib) manufacturing process (2), it is preferable that a usage of the base is much more excessive than that of the compound (Iba), for example, the usage of the base is preferably 10 to 150 mole times the compound (Iba).

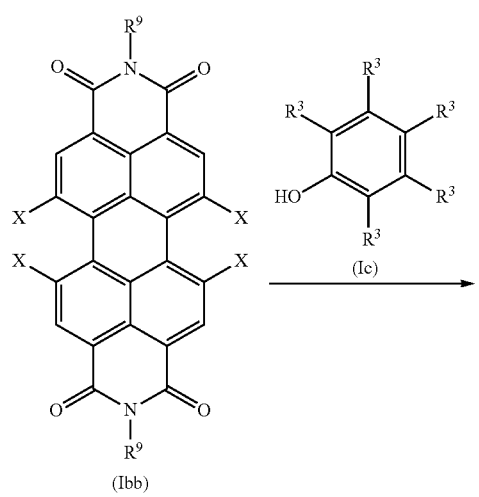
(Ibb)

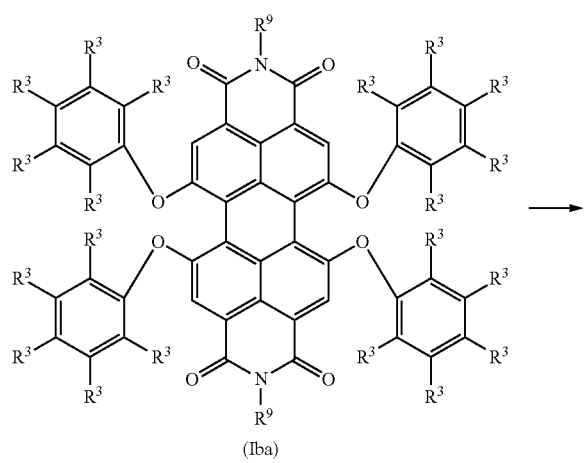
(Iba)

In the compound (Ib) manufacturing process (2), after the reaction is completed, the compound (Ib) may be taken out or the taken compound (Ib) may be refined by using a similar method to in a case of the compound (Ib) manufacturing process. Additionally, after the reaction is completed, and then post-treatment is performed as necessary, subsequently the next manufacturing process may be performed without taking out of the compound (Ib).

A structure of a product in each process, such as the compound (I) and the compound (Ib) may be confirmed by using the well-known method such as nuclear magnetic resonance (NMR) spectroscopy, mass spectrometry (MS), infrared spectroscopy (IR), and ultraviolet-visible spectroscopy (UV-VIS absorption spectrum), for example.

<Solar Cell Module>

A characteristic of the solar cell module according to the present invention is that the compound (I) is used. The solar cell module may have a structure in which the compound (I) absorbs sunlight, emission light from the compound (I), which is generated by absorption of the sunlight is concentrated, and the concentrated light is introduced into a solar cell element.

It is preferable that such a solar cell module includes a light guide and a solar cell element. The light guide has a light incident surface and a light exit surface having an area smaller than the light incident surface. The solar cell element receives exiting light from the light exit surface and thus generates electrical power. The light guide may contain the compound (I) and use emission light from the compound (I), which is resulted from absorption of the incident light from the light incident surface by the compound (I), as the exiting light.

The solar cell module according to the present invention has excellent power production by using the compound (I).

The solar cell module according to the present invention will be described below in detail with reference to the accompanying drawings. In the accompanying drawings, components are illustrated so as to have a recognizable size, and thus the scale of the components is appropriately changed.

Figure 2:
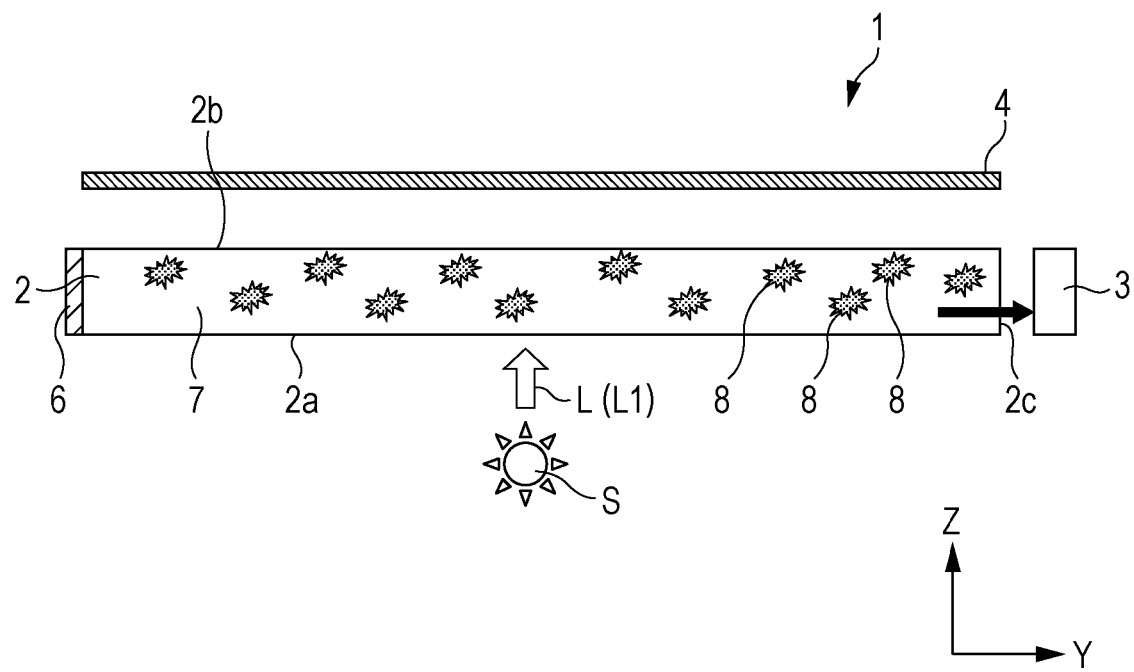
FIG. 2 is a cross-sectional view of the solar cell module according to the present invention.

FIG. 1 is a schematic diagram illustrating an overall configuration of the solar cell module according to an embodiment of the present invention. FIG. 2 is a cross-sectional view of the solar cell module.

The solar cell module 1 illustrated in FIG. 1 includes a light concentrating plate 2, a solar cell element 3, a reflective plate (reflector) 4, and a frame body 5. The light concentrating plate 2 has a rectangular shape and is installed so as to face the sun S. The solar cell element 3 is provided at an end face of the light concentrating plate 2. The reflective plate 4 is provided on a back surface side of the light concentrating plate 2.

The light concentrating plate 2 is a light guide that introduces the exiting light into the solar cell element 3. The solar cell element 3 receives the exiting light which exits from a first end face 2c of the light concentrating plate 2. The frame body 5 integrally holds the light concentrating plate 2 and the solar cell element 3.

The light concentrating plate 2 has a principal surface 2a functioning as the light incident surface, a back surface 2b on an opposite side of the principal surface 2a, the first end face 2c functioning as the light exit surface, and other end faces, as illustrated in FIGS. 1 to 2. In this embodiment, a reflective layer 6 is provided on end faces other than the first end face 2c.

In the light concentrating plate 2, the first end face 2c has an area smaller than that of the principal surface 2a, and thus concentration efficiency for the solar cell element 3 increases and power production of the solar cell module 1 increases.

In the light concentrating plate 2, phosphors 8 are dispersed in a transparent substrate 7, as illustrated in FIG. 2.

The transparent substrate 7 is formed of an organic material having high transparency, such as acrylic resin (such as polymethyl methacrylate (PMMA)), and polycarbonate; inorganic material having high transparency, such as glass, and the like.

In order to effectively take in external light, the transparent substrate 7 may have transmittance of 90% or more, more preferably 93% or more, for light in the wavelength range of 360 nm to 800 nm. From a view in that light having a wide wavelength range has high transmittance, an example of the transparent substrate 7 may preferably include a substrate formed of acrylic resin such as PMMA, a silicon resin substrate, a quartz substrate, and the like.

In this embodiment, the compound (I) is used as the phosphor 8.

The phosphors 8 are dispersed substantially uniformly in the transparent substrate 7.

One type of the compound (I) may be independently used or two types or more of the compound (I) may be used together.

As the phosphor 8, another well-known phosphor may be used together in addition to the compound (I).

As the phosphor other than the compound (I), an optical functional material that absorbs ultraviolet light or visible light and emits visible light or infrared light may be included. Visible light is light in the wavelength range from 380 nm to 750 nm; ultraviolet light is light in the wavelength range less than 380 nm; and infrared light is light in the wavelength range greater than 750 nm.

The phosphor other than the compound (I) may be either of an inorganic phosphor and an organic phosphor.

Examples of the organic phosphor include coumarin-based dyes, perylene-based dyes, phthalocyanine-based dyes, stilbene-based dyes, cyanine-based dyes, polyphenylene-based dyes, xanthene-based dyes, pyridine-based dyes, oxazine-based dyes, chrysene-based dyes, thioflavin-based dyes, pyrene-based dyes, anthracene-based dyes, acridone-based dyes, acridine-based dyes, fluorene-based dyes, terphenyl-based dyes, ethene-based dye, butadiene-based dyes, hexatriene-based dyes, oxazole-based dyes, diphenylmethane-based dyes, triphenylmethane-based dyes, thiazole-based dyes, thiazine-based dyes, naphthalimide-based dyes, and anthraquinone-based dyes.

More specifically, examples of the organic phosphor include coumarin-based dyes such as 3-(2'-benzothiazolyl)-7-diethylamino coumarin (coumarin 6), 3-(2'-benzimidazolyl)-7-N, N-diethylaminocoumarin (Coumarin 7), 3-(2'-N-methyl-benzimidazolyl)-7-N,N-diethylaminocoumarin (coumarin 30), and 2,3,5,6-1H,4H-tetrahydro-8-trifluoromethyl-Kino lysine (9,9a,1-gh) coumarin (coumarin 153); Basic Yellow 51 being the coumarin-based dye; naphthalimide-based dyes such as Solvent Yellow 11 and Solvent Yellow 116; rhodamine-based dyes such as rhodamine B, rhodamine 6G, rhodamine 3B, rhodamine 101, rhodamine 110, sulforhodamine, Basic Violet 11, and Basic Red 2; pyridine-based dyes such as 1-ethyl-2-[4-(p-dimethylaminophenyl)-1,3-butadienyl]pyridinium-perchlorate (pyridine 1); cyanine-based dyes; oxazine-based dyes, and the like.

In addition to these substances, a substance having fluorescence among various dyes such as a direct dye, an acid dye, a basic dye, and a disperse dye may be also used.

Examples of the inorganic phosphor include a red light-emitting phosphor such as $GdBO_3$:Eu, $Gd_2O_3$:Eu, $Gd_2O_2S$:Eu, $Gd_3Al_5O_{12}$:Eu, $Gd_3Ga_5O_{12}$:Eu, $GdVO_4$:Eu, $Gd_3Ga_5O_{12}$:Ce, Cr, $Y_2O_3$:Eu, $Y_2O_2S$:Eu, $La_2O_3$:Eu, $La_2O_2S$:Eu, $InBO_3$:Eu, and $(Y,In)BO_3$:Eu; a green light-emitting phosphor such as $Gd_2O_3$:Tb, $Gd_2O_2S$:Tb, $Gd_2O_2S$:Pr, $Gd_3Al_5O_{12}$:Tb, $Gd_3Ga_5O_{12}$:Tb, $Y_2O_3$:Tb, $Y_2O_2S$:Tb, $Y_2O_2S$:Tb,Dy, $La_2O_2S$:Tb, ZnS:Cu, ZnS:Cu,Au, $Zn_2SiO_4$:Mn, $InBO_3$:Tb, $MgGa_2O_4$:Mn; a blue light-emitting phosphor such as $YAlO_3$:Ce, $Y_2SiO_5$:Ce, $Gd_2SiO_5$:Ce, $YTaO_4$:Nb, BaFCl:Eu, ZnS:Ag, $CaWO_4$, $CdWO_4$, $ZnWO_4$, $MgWO_4$, $Sr_5(PO_4)_3Cl$:Eu, and $YPO_4$:Cl.

One type of the phosphor other than the compound (I) may be independently used or two types or more of the phosphor other than the compound (I) may be used together.

When two types or more of phosphor 8 are used together, a configuration in which energy transfer occurs between these phosphors 8 by the Foerster mechanism, and light emitted from the phosphor 8 having a longest peak wavelength in an emission spectrum functions as the exiting light directed to the solar cell element 3 may be made. In this case, the compound (I) may be used as one or more types among multiple types of the phosphors 8 which are used together, and any type of the phosphor 8 may be used as the compound (I) by selection.

The Foerster mechanism is direct movement of excitation energy between two adjacent phosphors due to resonance between electrons without undergoing the process of light emission and absorption. Since energy transfer between phosphors occurs without involving the light emission and absorption process, energy transfer efficiency may be substantially 100%, and energy loss is small under optimal conditions. Thus, the Foerster mechanism contributes to improvement in generation efficiency of a solar cell module. In order to reduce energy loss and to generate electrical power with high efficiency, for example, the phosphors 8 used together, in the transparent substrate 7 may have high density.

Energy transfer occurring due to the Foerster mechanism also occurs in a non-luminous material which is excited by external light but deactivates without emitting light, in addition to a light-emitting material such as the phosphor. Accordingly, such a non-luminous material may be used as the optical functional material in addition to the phosphor 8, and thus the non-luminous material may be dispersed in the transparent substrate 7.

A proportion of the occupying compound (I) for the total amount of the phosphors 8 in the transparent substrate 7 is preferably equal to or greater than 5 wt % such that the concentration efficiency for the solar cell element 3 increases and power production of the solar cell module 1 increases. It is preferable that the proportion is appropriately controlled in accordance with the number of other phosphors which are used along with the compound (I), a light absorption peak wavelength, and the like.

The light concentrating plate 2 in which the phosphors 8 are dispersed in the transparent substrate 7 is obtained in such a manner that a resin composition which contains raw material monomers constituting the transparent substrate 7, the phosphor 8 is prepared, and the resin composition is cured in a state where the phosphors 8 are dispersed. A curing method of the resin composition may be selected in accordance with the type of the raw material monomer.

In the light concentrating plate 2, the content of the phosphors 8 is preferably in a range of 0.001 wt % to 0.04 wt % against the transparent substrate 7. The content of the phosphors 8 is equal to or greater than the lower limit value, and thus an absorbed dose of sunlight in the light concentrating plate 2 is improved and the power production of the solar cell module 1 increases. The content of the phosphors 8 is equal to or less than the upper limit value, and thus the concentration efficiency for the solar cell element 3 is improved and the power production of the solar cell module 1 increases.

The principal surface 2a and the back surface 2b of the light concentrating plate 2 are parallel with each other and are flat surfaces. The reflective layers 6 are provided at all end faces of the light concentrating plate 2 except for the first end face 2c. The reflective layers 6 are provided so as to come into contact with the light concentrating plate 2 through an air space or so as to directly come into contact with the light concentrating plate 2 without the air space. Each of the reflective layers 6 causes light (light emitted from the phosphors 8) traveling outwardly from the inside of the light concentrating plate 2 to be directed into the light concentrating plate 2, and be reflected.

An example of the reflective layer 6 includes a reflective layer formed by using a film made of metal such as silver and aluminium; a reflective layer formed by using a dielectric multilayer such as an ESR (Enhanced Specular Reflector) reflective film (manufactured by 3M corporation). The reflective layer may be a specular reflective layer or a scattering reflective layer. The mirror reflective layer causes light which has been incident to perform specular reflection. The scattering reflective layer causes light which has been incident to perform scattering reflection. When the scattering reflective layer is used as the reflective layer, light intensity of light directly directed to a direction of the solar cell element 3 increases. Thus, the concentration efficiency for the solar cell element 3 increases and the power production of the solar cell module 1 increases more. Since reflected light is scattered, variation in power production due to the time or the seasons is averaged. As the scattering reflective layer, a layer formed of microformed PET (polyethylene terephthalate) (manufactured by Furukawa Electric Co., Ltd) may be included.

The reflective plate 4 may be similar to the reflective layer 6 except for a different shape.

The reflective plate 4 may reflect a portion of incident light L1 which has been incident to the light concentrating plate 2 among rays from the sun S (sunlight L) in a predetermined direction on an incident light path side of the incident light L1 (sunlight L) against a normal line of the principal surface 2a of the light concentrating plate 2, so as to be reflected light.

The concentration efficiency for the solar cell element 3 increases and the power production of the solar cell module 1 increases more by providing the reflective plate 4.

An example of the reflective plate 4 that reflects the portion of the incident light L1 in the predetermined direction so as to be the reflected light may include a retro-reflective plate and an off-axis reflective plate.

An example of the retro-reflective plate includes a reflective plate having a prism layer (corner-cube array) having multiple prism shapes. Three flat surfaces are formed on a surface of a substrate formed of resin, with an air space interposed between the flat surface and the substrate, and thereby the prism shape is formed. Examples of a commercial product include a high intensity grade HIP high brightness reflective sheet, a diamond grade DG ultra-high brightness reflective sheet (which are manufactured by 3M Corporation), and a prism type ultra-high brightness retro-reflective sheet (manufactured by Nippon Carbide Industries).

An example of the retro-reflective plate includes a reflective plate having a configuration in which incident light is refracted by glass beads, is reflected to a reflective layer on a back side, and then turns back in a direction in which the light has been incident. Examples of a commercial product include an engineer grade EGP usually reflective sheet (manufactured by 3M Corporation), an enclosed lens retro-reflective sheet, an encapsulated lens retro-reflective sheet (which are manufactured by Nippon Carbide Industries), and the like.

Examples of the off-axis reflective plate include a reflective plate obtained in such a manner that a prism shape is applied to one surface of a substrate such as an acrylic plate, a reflective material such as aluminium and silver is evaporated on this prism surface and thus a reflective surface is obtained and the surface is coated with a transparent protective layer; a reflective plate formed of a dielectric multilayer film which is obtained in such a manner that a high refractive index layer and a low refractive index layer are alternately layered by using the thickness of an optical layer corresponding to a ¼ wavelength, as an interval, and then the dielectric multilayer film is sliced (cut) at a predetermined angle; and a reflective plate in which reflective plate-shaped particles are arranged in a predetermined direction in a transparent substrate.

It is preferable that a light-receiving surface of the solar cell element 3 is disposed so as to face the first end face 2c of the light concentrating plate 2 and the light-receiving surface optically adheres to the first end face 2c.

The solar cell element 3 may be any of well-known solar cells, including a silicon-based solar cell, a compound-based solar cell, a quantum dot solar cell, and an organic solar cell. A compound-based solar cell using a compound semiconductor or a quantum dot solar cell is preferable for the solar cell element 3 since these solar cells can generate electric power with much higher efficiency.

As the compound-based solar cell, solar cells using InGaP, GaAs, InGaAs, AlGaAs, $Cu(In,Ga)Se_2$, $Cu(In,Ga)(Se,S)_2$, $CuInS_2$, CdTe, and CdS may be used.

As the quantum dot solar cell, solar cells using Si and InGaAs may be used.

However, in accordance with a price or a purpose, other solar cells such as a silicon-based solar cell and an organic-based solar cell may be preferable.

FIGS. 1 to 2 illustrate an example in which the solar cell element 3 is provided at only one first end face 2c of the light concentrating plate 2. However, the solar cell element 3 may be installed at a plurality of end faces of the light concentrating plate 2. When the solar cell element 3 is installed at end faces (first side, second side or third side) of the light concentrating plate 2, it is preferable that the reflective layer 6 is installed at end faces on which the solar cell element 3 is not installed.

The frame body 5 as illustrated in FIG. 2 is formed from a frame which is made of aluminium and the like. The frame body 5 holds four circumferences of the light concentrating plate 2 in a state where the principal surface 2a of the light concentrating plate 2 faces the outside, and holds the solar cell element 3 along with the light concentrating plate 2. A transparent member such as glass may be fit into an opening portion 5a which causes the principal surface 2a of the light concentrating plate 2 to face the outside. With such a configuration, the principal surface 2a which faces the outside from the frame body 5 functions as the light incident surface and the first end face 2c of the light concentrating plate 2 functions as the light exit surface in the light concentrating plate 2. A portion of external light (sunlight) which has been incident from the principal surface 2a transmits through the back surface 2b and thus is incident on the reflective plate 4.

In the solar cell module 1, the principal surface 2a of the light concentrating plate 2 is installed so as to face the sun S, as illustrated in FIGS. 1 to 2. The solar cell module 1 receives a portion of light (sunlight L) from the sun S as the incident light L1 on the principal surface 2a of the light concentrating plate 2, causes the phosphors 8 in the light concentrating plate 2 to absorb the incident light L1, and thus causes the phosphors 8 to emit light. The emission light from the phosphors 8, which is generated at this time propagates through the transparent substrate 7 of the light concentrating plate 2, exits from the first end face 2c, and thus is introduced into the solar cell element 3. In this manner, receiving of the exiting light causes the solar cell element 3 to generate electrical power.

In this embodiment, a plate in which the phosphors 8 are dispersed in the transparent substrate 7 and which is used as the light concentrating plate 2 is described. However, the light concentrating plate is not limited to such a configuration, and may have a configuration illustrated in FIG. 3A or 3B, for example.

Figure 3A:
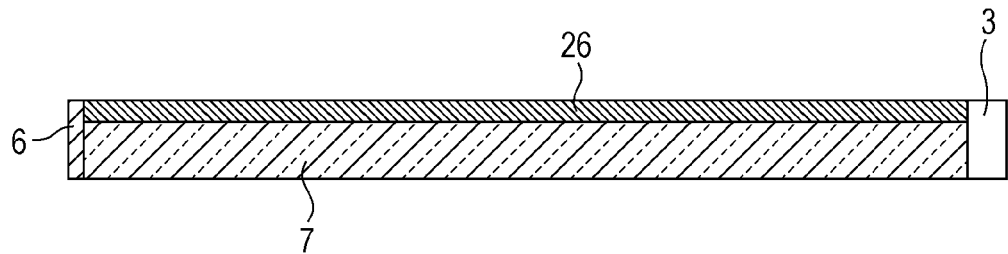
FIG. 3A is a side cross-sectional view illustrating a modification example of a light concentrating plate in the solar cell module according to the present invention.

In the light concentrating plate illustrated in FIG. 3A, the surface of the plate-like transparent substrate 7 which is formed from an acrylic plate and the like is coated with a coating material in which phosphors (not illustrated) are dispersed, and thereby a fluorescent layer 26 is formed. The coating material contains phosphors and transparent resin which causes the phosphors to be dispersed. That is, the transparent resin in this coating material becomes the transparent substrate in which phosphors are caused to be uniformly dispersed.

Figure 3B:
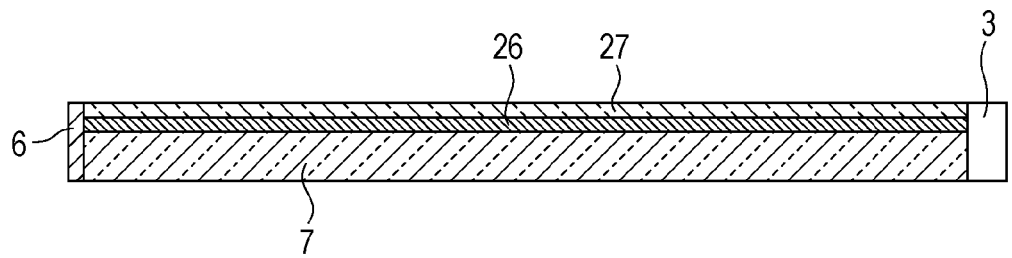
FIG. 3B is a side cross-sectional view illustrating a modification example of the light concentrating plate in the solar cell module according to the present invention.

In the light concentrating plate illustrated in FIG. 3B, a transparent protective layer (transparent layer) 27 is provided on a surface of the fluorescent layer 26 (surface on an opposite side of the transparent substrate 7).

As a material of the transparent protective layer 27, various types of transparent resin may be included. For example, the transparent protective layer 27 may be formed by laminating a transparent resin film on the fluorescent layer 26. The transparent resin film is formed of polyethylene terephthalate (PET), polyethylene (PE), polyvinylidene chloride, polyamide, or the like. The transparent protective layer 27 may be also formed in such a manner that a cellulose derivative or transparent resin is dissolved, and thereby a coating liquid is prepared, the prepared coating liquid is applied on the fluorescent layer 26 and then a result of application is dried. Examples of the cellulose derivative include cellulose acetate, ethyl cellulose and cellulose acetate butyrate. Examples of the transparent resin include polyvinyl chloride, polyvinyl acetate, vinyl chloride-vinyl acetate copolymers, polycarbonates, polyvinyl butyral, polymethyl methacrylate, polyvinyl formal, polyurethane.

Figure 4A:
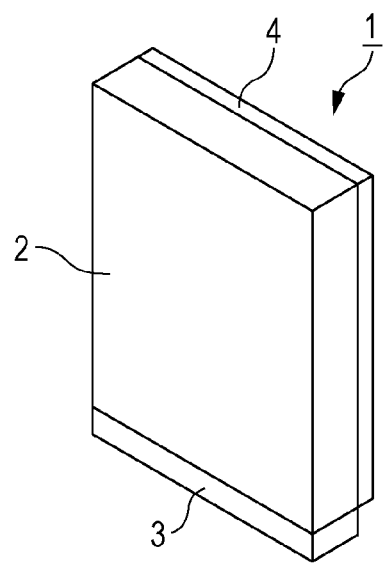
FIG. 4A is a perspective view illustrating a modification example of the solar cell module according to the present invention.

The solar cell module 1 according to this embodiment is installed on a side wall surface of a building, which is configured from a flat surface. The solar cell module 1 is configured such that the entirety of the solar cell module 1 has a flat shape by using the flat light concentrating plate 2 and the flat reflective plate (reflector) 4, as illustrated in FIG. 4A. However, the entire shape of the solar cell module may be adjusted in accordance with a shape and the like of an installation surface.

Figure 4B:
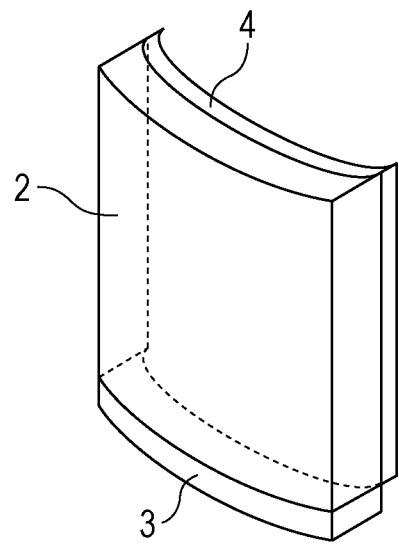
FIG. 4B is a perspective view illustrating a modification example of the solar cell module according to the present invention.

As a solar cell module other than such a flat solar cell module, a curved-plate solar cell module in which the entirety of the solar cell module is curved corresponding to a curved side surface of a building, as illustrated in FIG. 4B, may be included.

In this case, as illustrated in FIGS. 3A and 3B, the light concentrating plate 2 in which a coating material in which phosphors are dispersed is applied on a surface of a transparent substrate, and thereby a fluorescent layer is formed is preferable. The transparent substrate is formed so as to have a desired curved shape (curved plate shape), and thus the fluorescent layer having a desired curved shape may be formed on a surface of the transparent substrate. As the reflective plate, a plate in which a substrate is formed so as to have a desired curved shape (curved plate shape) and a recursive sheet sticks to a surface of the substrate may be included.

The curved plate-like light concentrating plate may be installed on a flat wall surface of a building. In this case, the reflective plate may have a curved plate shape or a flat plate shape.

The solar cell module may be installed on a roof of a building, a column, a utility pole, and the like. For example, when the solar cell module is installed on the roof, the light concentrating plate or the reflective plate may formed so as to have a tile shape, a wave shape, or the like and the entirety of the solar cell module may formed so as to have a tile shape, a wave shape, or the like by using the similar method to a case of the curved light concentrating plate illustrated in FIG. 4B.

Figure 4C:
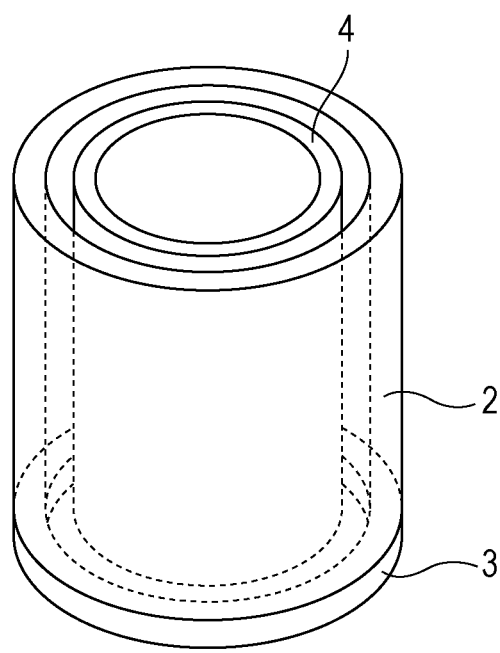
FIG. 4C is a perspective view illustrating a modification example of the solar cell module according to the present invention.

When the solar cell module is installed on a column such as a utility pole, the solar cell module includes a hollow cylindrical (cylindrical) light concentrating plate 2, a hollow cylindrical (cylindrical) reflector 4, a hollow cylindrical (cylindrical) or ring-like solar cell element 3, as illustrated in FIG. 4C. The reflector 4 is disposed on an inner circumference surface side, and the solar cell element 3 is disposed on the end face of the light concentrating plate 2. It is preferable that the entirety of the components forms a hollow cylindrical (cylindrical) solar cell module, and this solar cell module is installed so as to be placed on the outside of the column. Regarding a shape of a hollow portion, a case where a shape in a direction perpendicular to an axis of the hollow portion is circular is described. However, the shape may be appropriately adjusted in accordance with a shape of a target which causes the solar cell module to be placed on the outside of the target, and the shape is not limited to a circular shape.

Figure 4D:
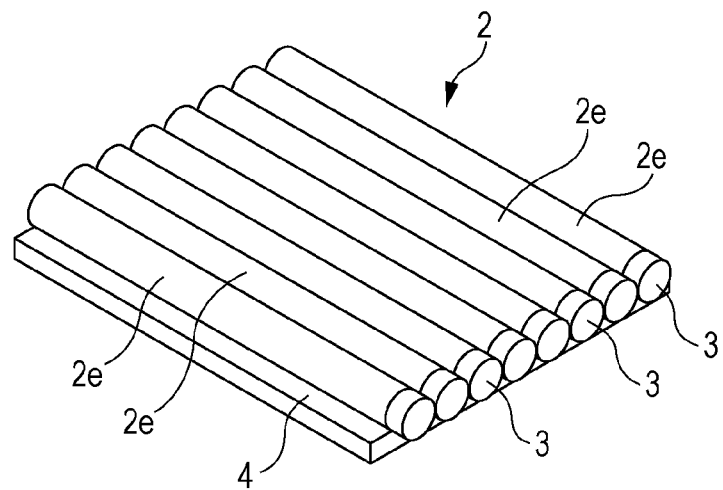
FIG. 4D is a perspective view illustrating a modification example of the solar cell module according to the present invention.

The light concentrating plate 2 having an appearance of a flat body may be installed by arranging cylindrical light concentrating members 2e on a flat surface in FIG. 4D. The solar cell element 3 is disposed at one end face (end portion) of the light concentrating member 2e. The light concentrating plate 2 may have a changeable shape, for example, not flat surface and a curved surface by flexibly linking the light concentrating members 2e to each other, and may be installed. In addition, the light concentrating plate 2 is configured to have a blind shape, and thus adjustment as follows may be performed. That is, the light concentrating plate 2 is unfolded and performs concentrating at a necessary time, and the light concentrating plate 2 is wound and stored at an unnecessary time.

Figure 5A:
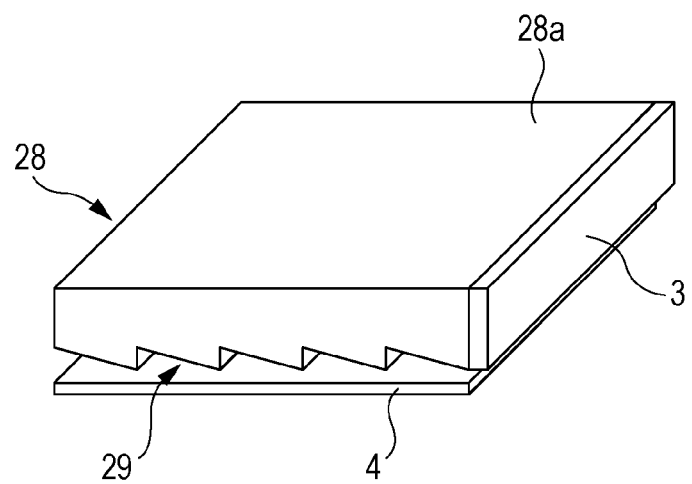
FIG. 5A is a perspective view illustrating a modification example of the solar cell module according to the present invention.
Figure 5B:
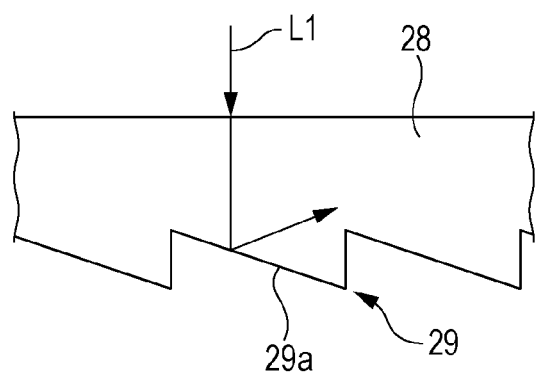
FIG. 5B is an enlarged view of a main component in FIG. 5A

As the light concentrating plate according to the present invention, a light concentrating plate 28 having a prism shape as illustrated in FIG. 5A may be used. This light concentrating plate 28 has a prism surface 29 on a back surface of an opposite side of the principal surface 28a which functions as the light incident surface. Since multiple slop surfaces 29a are formed toward one end face side as illustrated in FIG. 5B, on the prism surface 29, the incident light L1 is refracted on this slop surface 29a and thus exits to the solar cell element 3 which is disposed on the one end face side as illustrated in FIG. 5A. The emission light from the phosphors 8, which propagates similarly to such light L1 similarly exits to the solar cell element 3.

Figure 5C:
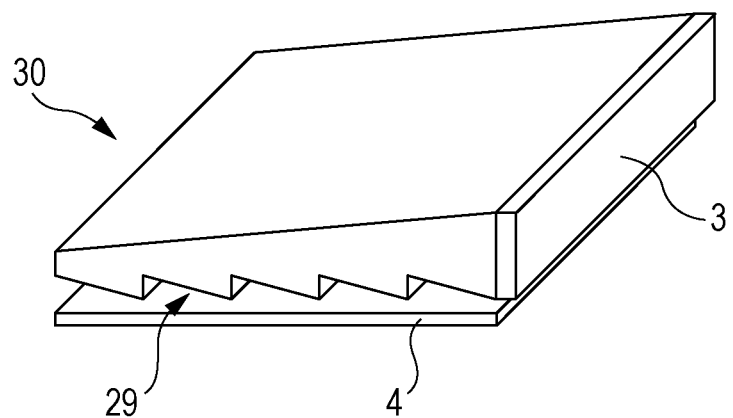
FIG. 5C is a perspective view illustrating a modification example of the solar cell module according to the present invention.

As the light concentrating plate according to the present invention, as illustrated in FIG. 5C, a wedge-like light concentrating plate 30 having the prism surface 29 may be used. The thickness of the light concentrating plate 30 becomes thinner as the light concentrating plate 30 is far away from the solar cell element 3. Formation in this manner causes the number of the incident light L1 and emission light from the phosphors 8 totally reflecting the inside of the light concentrating plate 30 to be reduced, and causes light loss occurring by refracting light on the slop surface 29a to be reduced in the light concentrating plate 30. Accordingly, light extraction efficiency increases.

Figure 5D:
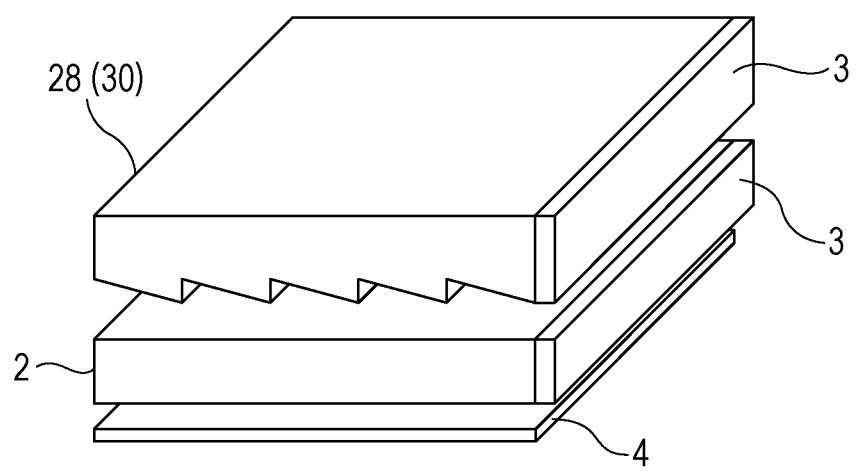
FIG. 5D is a perspective view illustrating a modification example of the solar cell module according to the present invention.

As the light concentrating plate in this invention, a plate having a tandem structure in which the light concentrating plate 2 and the shape light concentrating plate 28(30) having a prism shape are layered, as illustrated in FIG. 5D may be used. In this case, the shape light concentrating plate 28(30) having a prism shape may or may not contain compound (I).

<Photovoltaic Power Generation Device>

A photovoltaic power generation device according to the present invention includes the solar cell module according to the present invention.

FIG. 6 is a schematic configuration diagram of the photovoltaic power generation device according to an embodiment of the present invention.

The photovoltaic power generation device 1000 illustrated in FIG. 6 includes a solar cell module 1001, an inverter (DC/AC converter) 1004, and a storage battery 1005. The solar cell module 1001 converts sunlight energy from the sun S into electrical power. The inverter (DC/AC converter) 1004 converts direct current power output from the solar cell module 1001 into alternate current power. The storage battery 1005 stores the direct current power output from the solar cell module 1001.

The solar cell module 1001 is the above-described solar cell module according to the present invention, and includes a light concentrating member (light concentrating plate) 1002 for concentrating sunlight, and a solar cell element 1003 that generates power with sunlight concentrated by the light concentrating member 1002.

The photovoltaic power generation device 1000 supplies electrical power to an external electronic device 1006. The electronic device 1006 is supplied with electrical power by an auxiliary power source 1007 as necessary.

Since such a photovoltaic power generation device 1000 includes the above-described solar cell module according to the present invention, the photovoltaic power generation device 1000 has excellent generation efficiency.

EXAMPLES

The present invention will be described below in detail with specific examples, but the present invention is not limited to examples described as follows.

Manufacturing of Compound (I)

Example 1

As compound (I), compounds (abbreviated to a "compound (1A)-101" and a "compound (1B)-101") represented by the following formula (1A)-101 and (1B)-101 were manufactured through the following procedures.

(Compound (Iac) Manufacturing Process)

Phenyl boronic acid (56 g, 0.46 mol), 4-bromo-1,2-dimethoxybenzene (50 g, 0.23 mol), sodium carbonate (117 g, 1.10 mol), $PdCl_2(PPh_3)_2$ (5.0 g, 6.2 mmol), toluene (1000 ml), and water (930 ml) were inserted into a 2000 ml three neck flask under an argon gas flow.

Then, the temperature was increased until a reaction liquid was recirculated, and reaction was performed with stirring for 9 hours.

After the reaction was completed, the reaction liquid was cooled upto a room temperature and insoluble matters were removed by celite filtration. Then a filtrate was divided into two liquids. An organic layer was washed twice with water (500 ml) and was washed with a saturated salt solution (500 ml). Then, the organic layer was dehydrated by using anhydrous magnesium sulfate and active carbon filtration was performed. The obtained filtrate was concentrated and then adds ethanol, and thereby crystallization was performed. Crystals were taken out and dried. Thus, a compound (abbreviated to a "compound (1)-101ac") which was represented by the following formula (1)-101ac, as the compound (Iac) was obtained (collected amount: 26 g, and yield: 52.8%).

It was confirmed that the compound (1)-101ac was obtained, by NMR measurement or IR measurement. The compound (1)-101ac also corresponds to the compound (Iabc).

[Chem. 9]

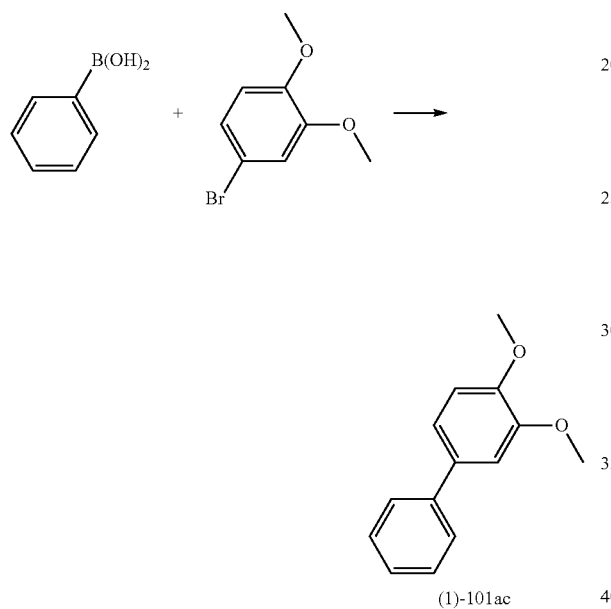

(1)-101ac

[Chem. 10]

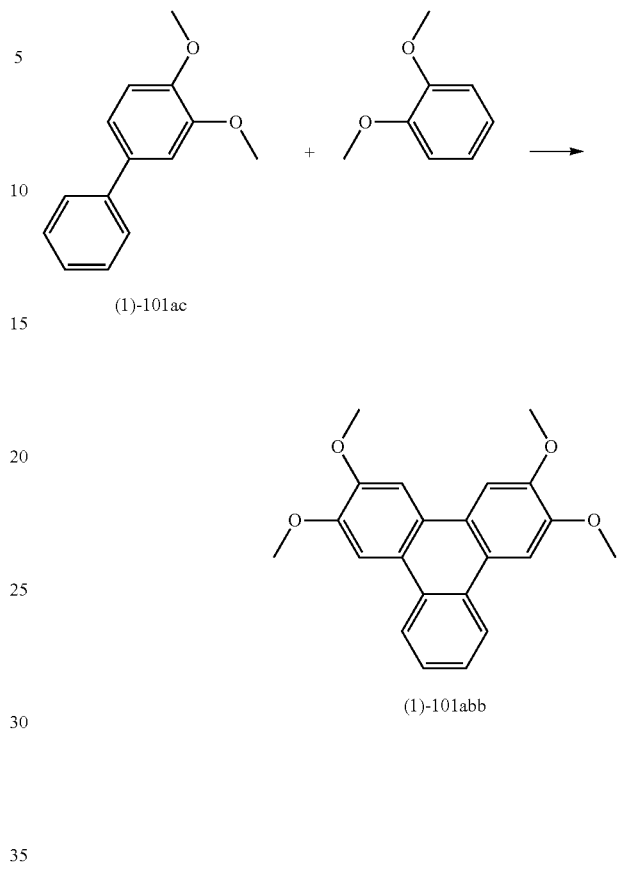

(1)-101ac (1)-101abb (Compound (Iabb) Manufacturing Process)

1,2-dimethoxybenzene (50 g, 0.36 mol), the compound (1)-101ac (19.3 g, 0.09 mol), iron chloride (III)(117 g, 0.72 mol), and dichloromethane (1250 ml) were inserted into a 2000 ml three neck flask, and reacted with each other with stirring for 2 hours at the room temperature.

After the reaction was completed, the reaction liquid was added to cool water (600 ml) and divided into two liquids. An organic layer was washed twice with water (500 ml) and was washed with a saturated salt solution. Then, the organic layer was dehydrated by using anhydrous magnesium sulfate and active carbon filtration was performed. The obtained filtrate was concentrated and then adds ethanol, and thereby crystallization was performed. Crystals were taken out, were subjected to slurry washing with ethanol, and then dried. Thus, a compound (abbreviated to a "compound (1)-101abb") which was represented by the following formula (1)-101abb, as the compound (Iabb) was obtained (collected amount: 17.2 g, and yield: 54.9%).

It was confirmed that the compound (1)-101abb was obtained, by MS measurement, NMR measurement, and IR measurement. For example, a spectrum of a pro-ion peak m/z=348 was confirmed in the MS measurement.

(Compound (Iaba) Manufacturing Process)

The compound (1)-101abb (9 g, 26 mmol), 47% hydrobromic acid (187 ml), and acetic acid (187 ml) were inserted into a 500 ml three neck flask.

Then, the temperature was increased until a reaction liquid was recirculated, and reaction was performed with stirring for overnight. At this time, the reaction liquid became a uniform liquid with progress of the reaction.

After the reaction was completed, the reaction liquid was cooled upto the room temperature and concentrated. Then, pH of concentrates was adjusted to 3 by using sodium hydrogen carbonate and extraction was performed with ethyl acetate. After an extraction liquid was washed three times with water (50 ml), and was washed with a saturated salt solution, activated carbon and anhydrous magnesium sulfate were added and stirred, and then filtration was performed. After the obtained filtrate was subjected to concentration, drying, and hardening, precipitated crystals were taken out and dried. Thus, a compound (abbreviated to a "compound (1)-101aba") which was represented by the following formula (1)-101aba, as the compound (Iaba) was obtained (collected amount: 7.4 g, and yield: 98.7%).

It was confirmed that the compound (1)-101aba was obtained, by NMR measurement and IR measurement. For example, performing of demethylation was confirmed in the NMR measurement, and —OH expansion and contraction vibration was confirmed in the IR measurement.

[Chem. 11]

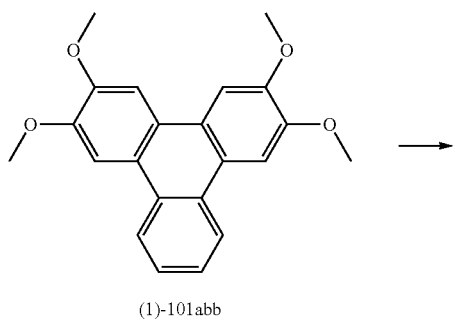

(1)-101abb

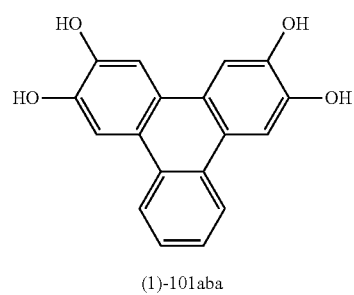

(1)-101aba

[Chem. 12]

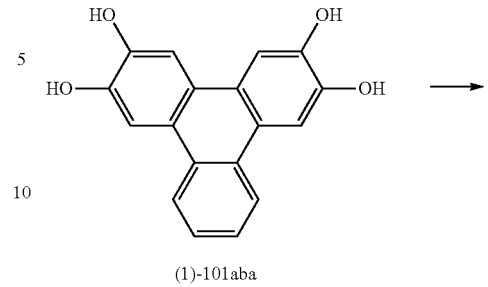

(1)-101aba

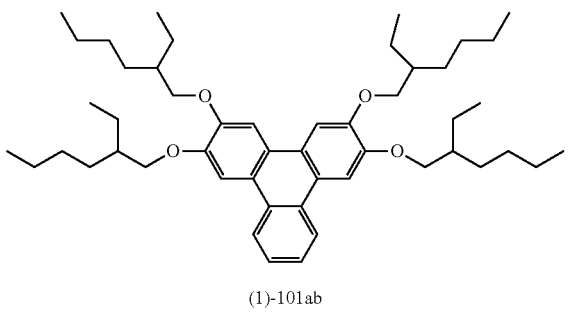

(1)-101ab (Compound (Iab) Manufacturing Process (2))

The compound (1)-101aba (5 g, 17.1 mmol), 1-bromo-2-ethyl hexane (19.8 g, 102.6 mmol), potassium carbonate (14.2 g, 102.6 mmol), N,N-dimethylformamide (DMF, 150 ml) were inserted into a 200 ml three neck flask.

Then, the temperature of the reaction liquid was increased up to 90° C., and reaction was performed with stirring for 5 hours.

After the reaction was completed, the reaction liquid was cooled up to the room temperature and was added to a solvent mixture of water (300 ml) and dichloromethane (100 ml) and then was divided into two liquids. A water layer was extracted with dichloromethane (50 ml). The extracted organic layer was added, and a result of addition was washed twice with water (50 ml), and then was washed with a saturated salt solution. Then, activated carbon and anhydrous magnesium sulfate were added and stirred, and then filtration was performed. The obtained filtrate was subjected to concentration, and column chromatography in which matters passes through a silica gel (65 g) was performed on concentration residues by using a solvent mixture of hexane/ethyl acetate (5/1, volume ratio). The obtained fraction was subjected to concentration, drying, and hardening, and thus a compound (abbreviated to a "compound (1)-101ab") which was represented by the following formula (1)-101ab, as the oil-like compound (Iab) was obtained (collected amount: 12.9 g, and yield: 101.5%).

It was confirmed that the compound (1)-101ab was obtained, by MS measurement, NMR measurement, and IR measurement. For example, a spectrum of a pro-ion peak m/z=741 was confirmed in the MS measurement, existing of a 2-ethylhexyloxy group was confirmed in the NMR measurement, and disappearing of —OH expansion and contraction vibration was confirmed in the IR measurement.

(Compound (Iaa) Manufacturing Process)

The compound (1)-101ab (12.4 g, 16.7 mmol) and dichloromethane (250 ml) were inserted into a 500 ml three neck flask and cooled up to a range of −5° C. to 0° C. A result obtained by dissolving bromine (16.0 g, 100.0 mmol) in dichloromethane (250 ml) was dropped in the cooled solution such that the temperature was equal to or lower than 0° C. After dropping was ended, stirring was performed for 2 hours and an end of the reaction was confirmed by thin-layer chromatography (TLC).

Then, a reaction liquid was added to a sodium thiosulfate solution, and stirred. Division into two liquids was performed, and an organic layer was washed twice with water (100 ml) and washed with a saturated salt solution (100 ml). Then, activated carbon and anhydrous magnesium sulfate were added and stirred, and then filtration was performed. The obtained filtrate was subjected to concentration, and column chromatography in which matters passes through a silica gel (300 g) was performed on concentration residues by using a solvent mixture of hexane/chloroform (9/1, volume ratio). Thus, impurities such as tribromo matters and tetrabromo matters were removed. Fractions (6 g) containing a target were dispersed in ethanol (30 ml), and a tar-like solid matter was taken and dried. Thus, a compound (abbreviated to a "compound (1)-101aa") which was represented by the following formula (1)-101aa, as the compound (Iaa) was obtained (collected amount: 4.6 g, and yield: 30.7%).

It was confirmed that the compound (1)-101aa was obtained, by MS measurement, NMR measurement, and IR measurement. For example, a spectrum of a pro-ion peak m/z=898 was confirmed in the MS measurement.

[Chem. 13]

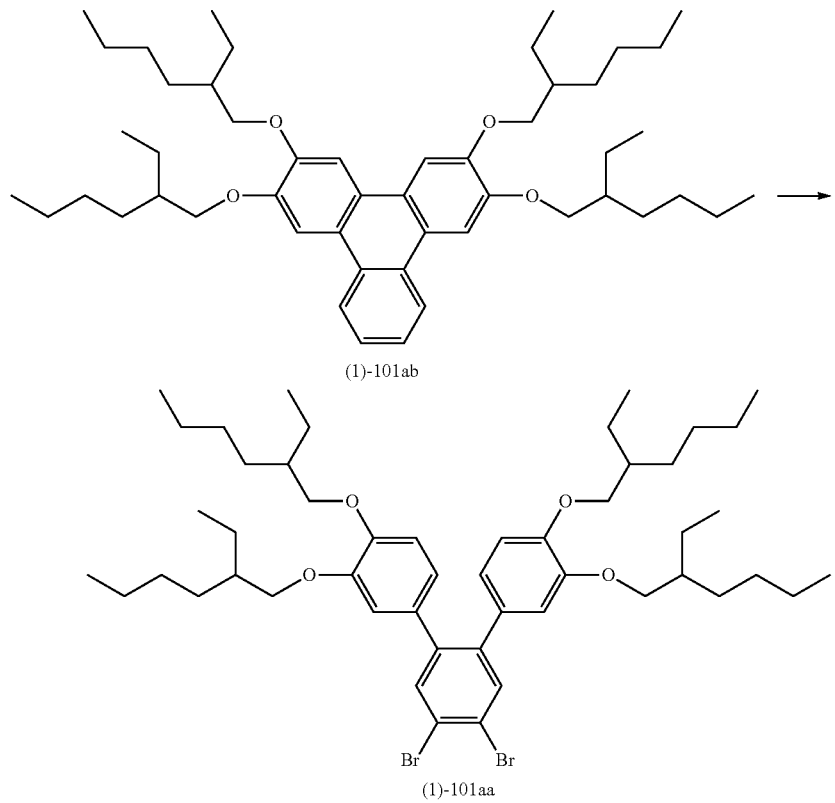

(Compound (Ia) Manufacturing Process)

Tris (dibenzylideneacetone) dipalladium (0.10 g, 0.11 mmol), rac-BINAP (0.14 g, 0.22 mmol), and toluene (140 ml) were inserted into a 200 ml three neck flask under a argon gas flow, and stirred at 110° C. for 30 minutes.

Then, a result of stirring was cooled up to the room temperature, and the compound (1)-101aa (4 g, 4.4 mmol), benzophenone imine (2.06 g, 11.4 mmol), and sodium t-butoxide (1.09 g, 11.4 mmol) were added to a result of cooling. The temperature was increased until a reaction liquid was recirculated, and reaction was performed with stirring for overnight.

After the reaction was completed, the reaction liquid was cooled up to the room temperature and insoluble matters were removed by celite filtration. Water (50 ml) was added to a mother liquid, stirred, and divided into two liquids. An organic layer was washed with water (50 ml) and washed with a saturated salt solution (50 ml). Then, activated carbon and anhydrous magnesium sulfate were added and stirred, and then filtration was performed. The obtained filtrate was subjected to concentration, concentration residues were dispersed in ethanol (35 ml) and thus crystals were taken and dried. Thus, the intermediate (2,3-benzophenone imine-6,7, 10,11-tetrakis(2-ethyl-hexyloxy)triphenylene) having two groups represented by a formula of "—N=C($C_6H_5$)$_2$" was obtained (collected amount 4.5 g, yield 93.7%).

It was confirmed that the intermediate was obtained, by NMR measurement and IR measurement. For example, it was confirmed that a ratio of the number of H of an alkyl group:the number of H of a benzene ring, in $^1$H-NMR measurement is 72.4:26.1.

The intermediate (4 g, 3.64 mmol), 2M hydrocholoric acid (3.8 ml, 7.64 mmol), and tetrahydrofuran (THF, 100 ml) were inserted into a 100 ml three neck flask and reaction was performed with stirring for 30 minutes.

After the reaction was completed, water (100 ml) and ethyl acetate (200 ml) were added to the reaction liquid and stirred, and then divided into two liquids. A water layer was extracted by using ethyl acetate (50 ml). The extracted organic layer was added, and a result of addition was washed with water (50 ml), and then was washed with a saturated salt solution (50 ml). Then, activated carbon and anhydrous magnesium sulfate were added and stirred, and then filtration was performed. The obtained filtrate was concentrated, and ethanol (50 ml) was added to the concentrated filtrate and dissolved. Several droplets of 25% sodium hydroxide aqueous solution were added, pH of the solution was adjusted to be a range of 9 to 10. Then, water and diethyl ether were added to a result of pH adjustment and stirred, and then extraction was performed. The obtained organic layer was washed with a saturated salt solution and then anhydrous magnesium sulfate was added. Thus, dehydration and concentration were performed. Column chromatography in which matters passes through a silica gel (60 g) was performed on concentration residues by using a solvent mixture of hexane/ethyl acetate (5/1, volume ratio). Fractions containing a target were concentrated, and thus a compound (abbreviated to a "compound (1)-101a") which was represented by the following formula (1)-101a, as the compound (Ia) was obtained (collected amount: 1.9 g, and yield: 61.9%).

It was confirmed that the compound (1)-101a was obtained, by MS measurement, NMR measurement, and IR measurement. For example, a spectrum of a pro-ion peak m/z=771 was confirmed in the MS measurement. It was confirmed that a ratio of the number of H of an alkyl group:the number of H of a benzene ring, in $^1$H-NMR measurement is 68.4:6 (ideal value is 68:6).

[Chem. 14]

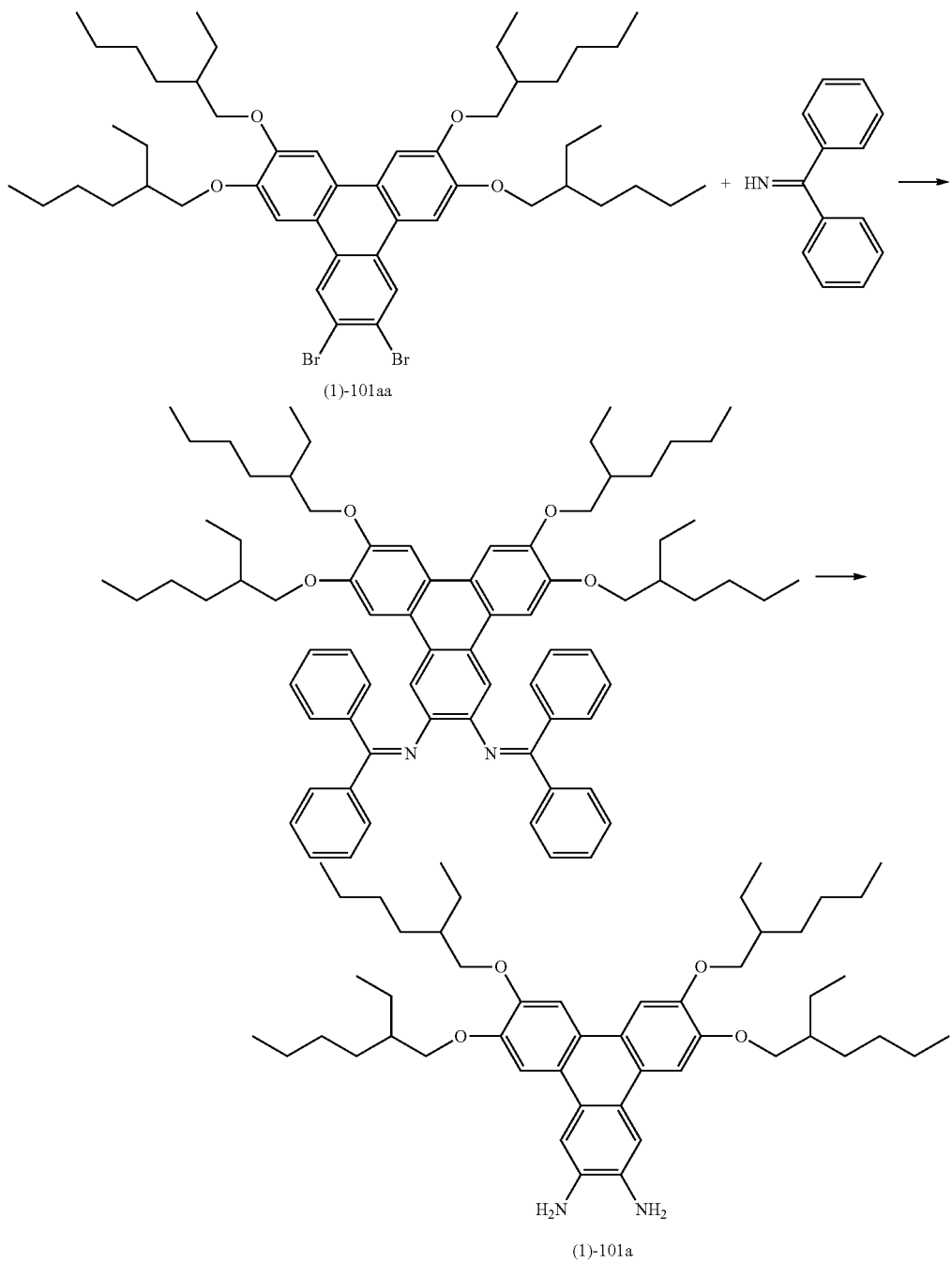

(Compound (Id) Manufacturing Process)

Chlorosulfuric acid (500 g, 4.29 mol) was inserted into a 1000 ml three neck flask under an argon gas flow. 3,4,9,10-perylene tetracarboxylic acid dianhydride (50 g, 0.127 mol) was added to the chlorosulfuric acid for 20 minutes at the room temperature and then iodine (8.5 g, 0.024 mol) was added.

Then, the temperature of the reaction liquid was increased up to 70° C., and reaction was performed with stirring for 6 hours.

After the reaction was completed, the reaction liquid was cooled such that the temperature became the room temperature, and quenching was performed with cool water (2000 ml). The reaction liquid was discolored from dark brown to scarlet and crystals were precipitated. These crystals were taken out, and subjected to slurry washing with water (1000 ml) three times. Then, slurry washing was performed three times with acetonitrile (500 ml), and taken crystals were dried. Thus, a compound (abbreviated to a "compound (1)-101d") which was represented by the following formula (1)-101d, as the compound (Id) was obtained (collected amount: 50.1 g, and yield: 74.4%).

It was confirmed that the compound (1)-101d was obtained, by MS measurement, ion chromatography, and IR measurement. For example, a spectrum of a pro-ion peak m/z=530 was confirmed in the MS measurement. It was confirmed that a chlorine content was 25.1% (ideal value: 26.8%) by using an oxygen combustion method in the ion chromatography.

[Chem. 15]

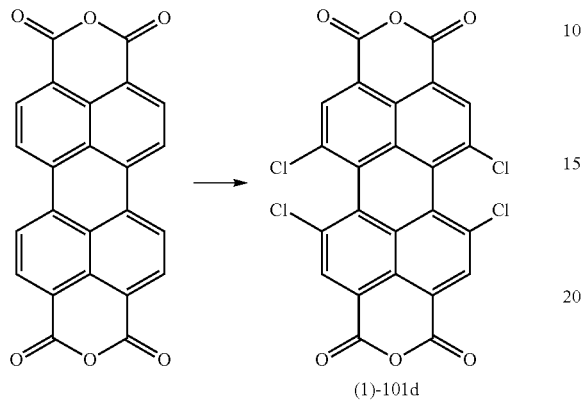

(1)-101d (Compound (Ibb) Manufacturing Process)

The compound (1)-101d (20 g, 37.7 mmol), n-pentylamine (13.1 g, 150.8 mmol), and propionic acid (225 g) were inserted into a 300 ml three neck flask.

The temperature of a reaction liquid increased up to 140° C. and the reaction was performed with stirring for 24 hours.

After the reaction was completed, the reaction liquid was cooled up to the room temperature. Crystals were precipitated and taken out. These crystals was subjected to slurry washing with a 10% sodium hydrogen carbonate aqueous solution (400 ml) and then was subjected to slurry washing with water (200 ml). The taken crystals were cleaned with methanol and dried. Thus, a compound (abbreviated to a "compound (1)-101bb") which was represented by the following formula (1)-101bb, as the compound (Ibb) was obtained (collected amount: 21.7 g, and yield: 86.1%).

It was confirmed that the compound (1)-101bb was obtained, by MS measurement, NMR measurement, and IR measurement. For example, a spectrum of a pro-ion peak m/z=668 was confirmed in the MS measurement, and existing of an n-pentyl group was confirmed in the NMR measurement.

[Chem. 16]

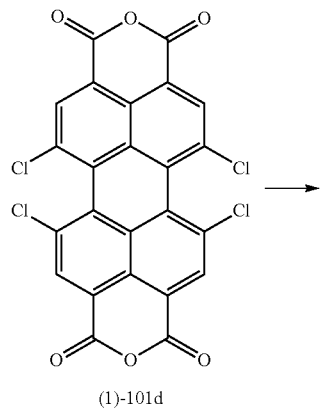

(1)-101d

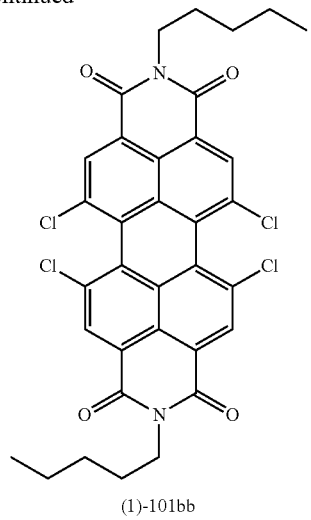

(1)-101bb (Compound (Iba) Manufacturing Process)

The compound (1)-101bb (20 g, 0.03 mol), a compound (4-dodecylphenol, below abbreviated to a "compound (1)-101c") (47.2 g, 0.18 mol) which was represented by the following formula (1)-101c, as the compound (Ic), potassium carbonate (24.8 g, 0.18 mol), and N-methylpyrrolidone (600 ml) were inserted into a 1000 ml three neck flask.

Then, the temperature of the reaction liquid increased up to 140° C. and the reaction was performed with stirring for 24 hours.

After the reaction was completed, the reaction liquid was cooled up to the room temperature, and added to 2N hydrocholoric acid. Thus, a tar-like solid matter was taken out and subjected to slurry washing with water (1000 ml), and then was subjected to slurry washing with methanol (1000 ml) twice. Thus, a tar-like solid matter was taken out (65 g in a wet state). This tar-like solid matter was dissolved in dichloromethane (300 ml) and filtered, and thereby the obtained filtrate was concentrated such that a liquid amount became substantially 200 ml. Then, column chromatography in which matters passes through a silica gel (250 g) was performed on concentration residues by using a solvent mixture of dichloromethane/hexane (1/1, volume ratio). Thus, a compound (abbreviated to a "compound (1)-101ba") which was represented by the following formula (1)-101ba, as the tar-like compound (Iba) was obtained (collected amount: 23.0 g).

It was confirmed that the compound (1)-101ba was obtained, by NMR measurement and IR measurement. For example, it was confirmed that a ratio of the number of H of an alkyl group:the number of H of a benzene ring, in $^1$H-NMR measurement is 123.76:20.02 (ideal value is 121:20).

[Chem. 17]

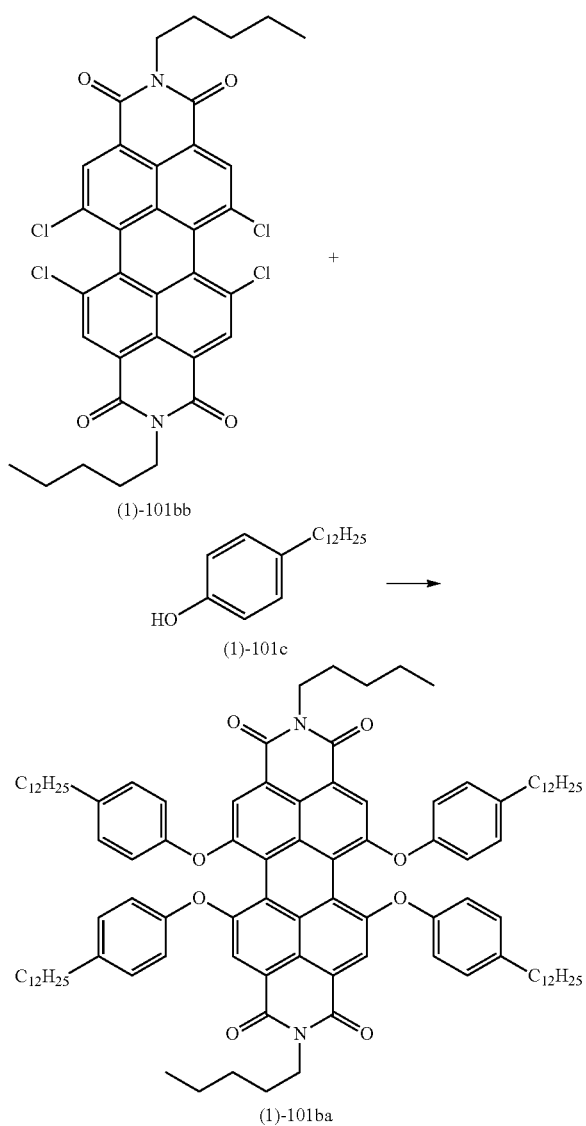

(Compound (Ib) Manufacturing Process (2))

The compound (1)-101ba (22 g, 14 mmol), 85% potassium hydroxide (98 g, 1490 mmol), and 2-propanol (220 m) were inserted into a 300 ml three neck flask.

Then, the temperature of the reaction liquid increased until recirculation was performed and the reaction was performed with stirring for 72 hours. At this time, the reaction liquid was discolored from reddish violet to green.

After the reaction was completed, the reaction liquid was cooled up to the room temperature and pH was adjusted to be 4 by using 8% hydrocholoric acid. Thus, a tar-like solid matter which had been precipitated was taken out and subjected to slurry washing with water (500 ml) twice, and then was subjected to slurry washing with methanol (500 ml) twice. Thus, a solid matter was taken out and dried at the room temperature. Thus, a compound (abbreviated to a "compound (1)-101b") which was represented by the following formula (1)-101b, as the compound (Ib) was obtained (collected amount: 14 g, and yield: 70%).

It was confirmed that the compound (1)-101b was obtained, by NMR measurement and IR measurement.

For example, it was confirmed that a ratio of the number of H of an alkyl group:the number of H of a benzene ring, in $^1$H-NMR measurement is 104.80:19.98 (ideal value is 100:20).

[Chem. 18]

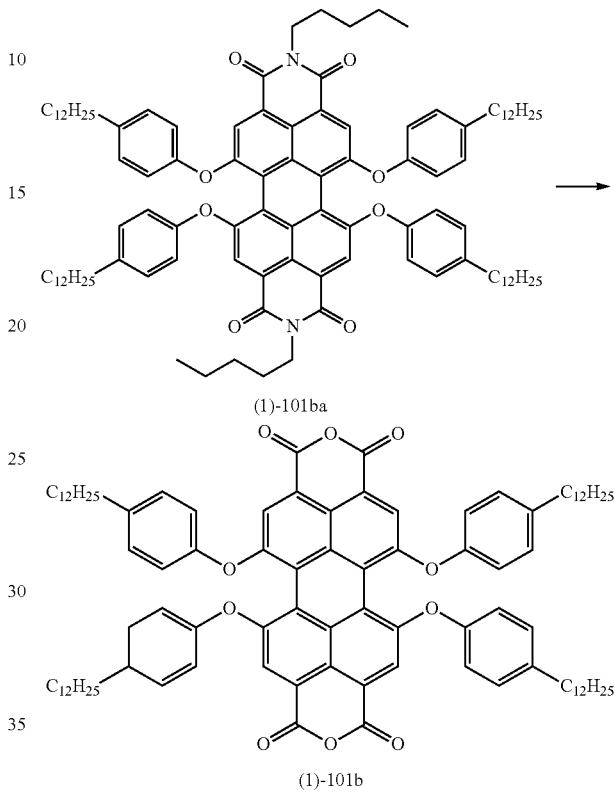

(Compound (I) Manufacturing Process)

The compound (1)-101b (0.75 g, 0.52 mmol), the compound (1)-101a (1.6 g, 2.08 mmol), pyrazine (0.16 g, 2.08 mmol), phenol (16 g), and toluene (16 ml) were inserted into a 100 ml three neck flask.

Then, the temperature of the reaction liquid increased, and water which was a byproduct in the system was discharged to the outside of the system by azeotropic dehydration with toluene. Phenol (16 g) was added at an effusion temperature of 100° C., and the temperature of the reaction liquid increased up to 145° C., and the reaction was performed with stirring for 24 hours.

After the reaction was completed, the reaction liquid was cooled up to the room temperature and added to methanol (160 ml). Thus, precipitated crystals were taken out, dissolved in dichloromethane (25 ml), and filtered. Then, column chromatography in which matters passes through a silica gel (120 g) was performed on the obtained filtrate by using a solvent mixture of dichloromethane/hexane (1/1, volume ratio). Fractions (0.9 g) containing a target were dissolved in dichloromethane (20 ml), and activated carbon was added to a result of dissolving and stirred. Then filtration was performed. The obtained filtrate was subjected to concentration, drying, and hardening, and thus the obtained solid matter was subjected to slurry washing with methanol, and dried at the room temperature. Thus, a mixture of the compounds (1A)-101 and (1B)-101 was obtained.

Figure 7:
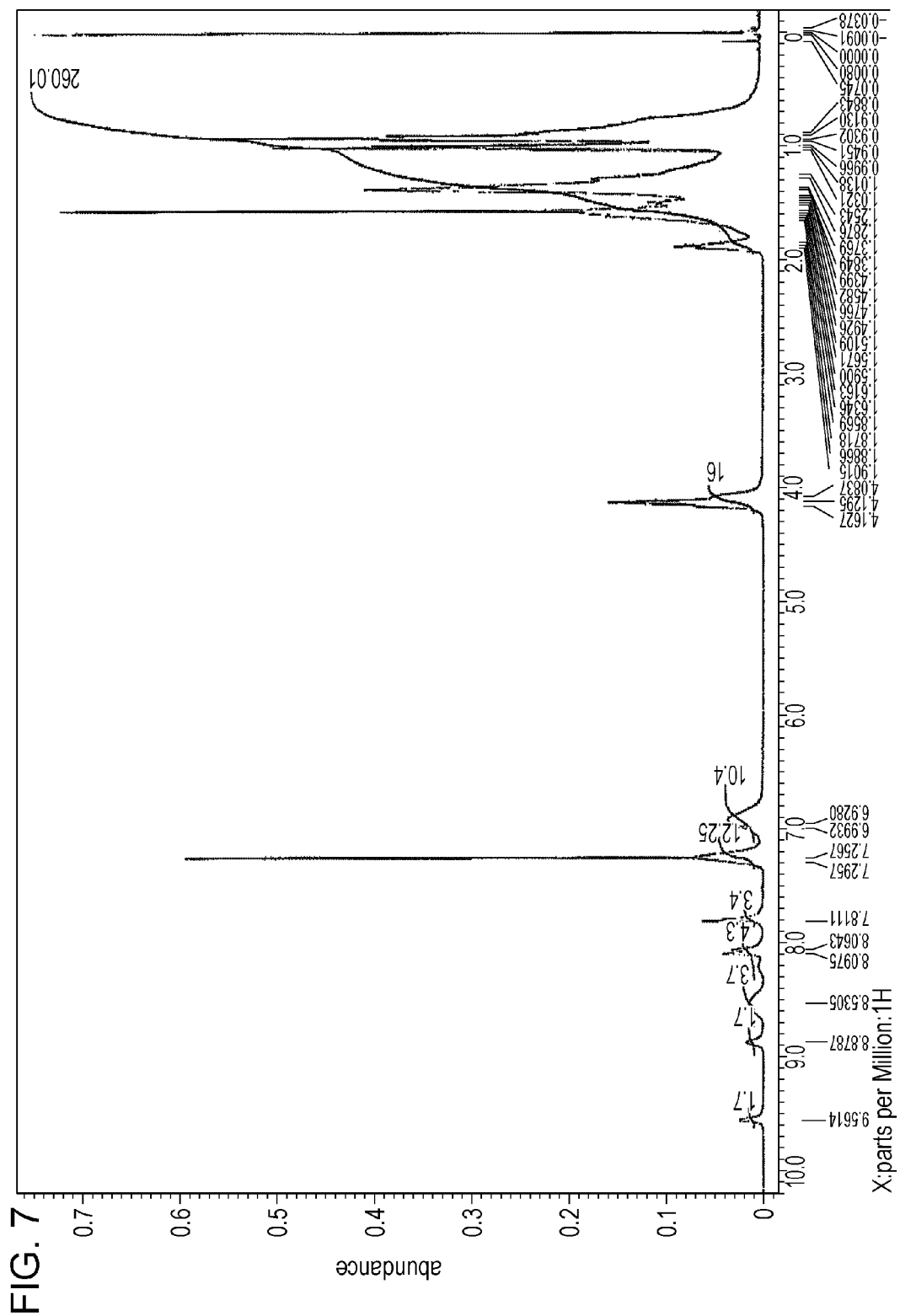
FIG. 7 is a $^1$H-NMR spectrum data of a compound (I) obtained in Example 1.
Figure 8:
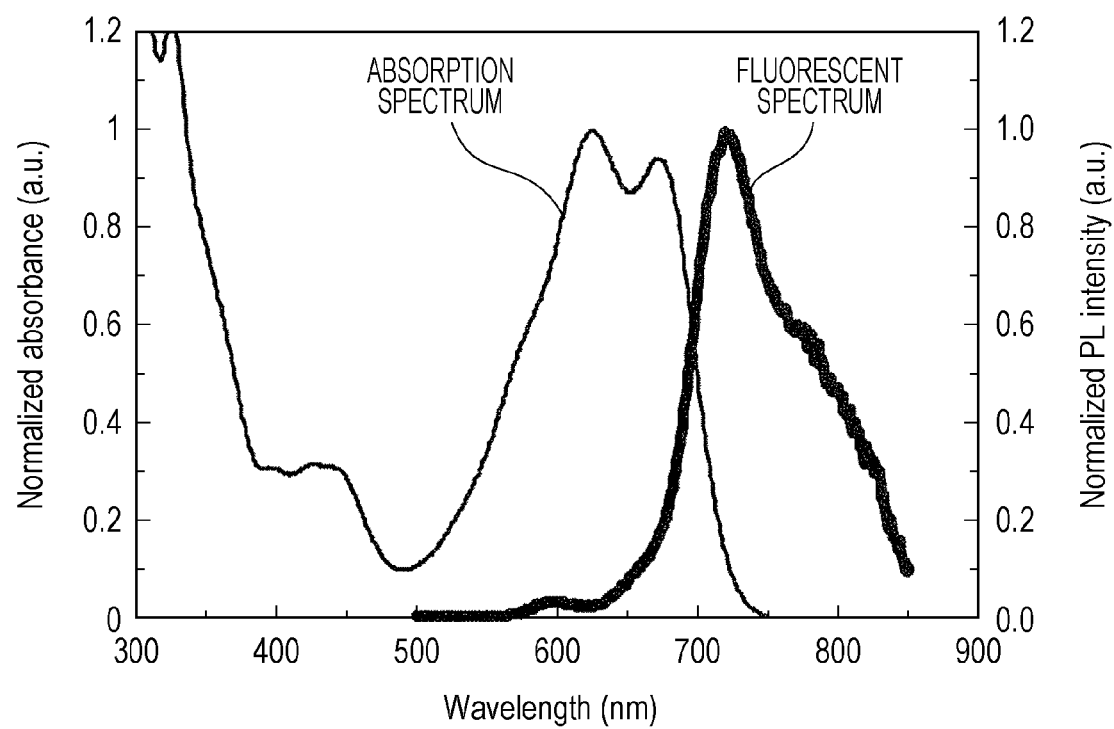
FIG. 8 is data of an UV-VIS absorption spectrum and a fluorescent light spectrum of the compound (I) obtained in Example 1.
Figure 9:
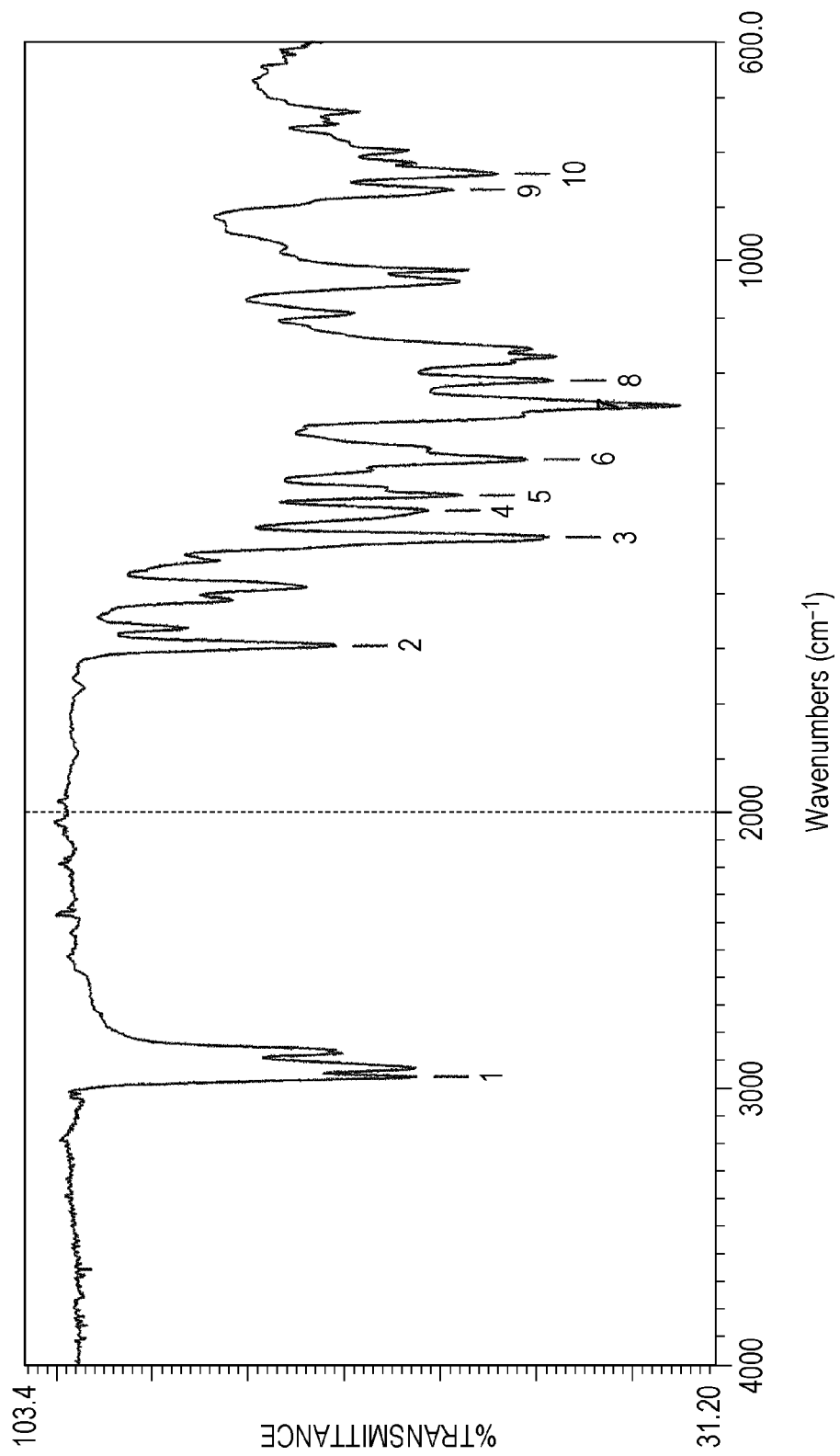
FIG. 9 is data of an IR spectrum of the compound (I) obtained in Example 1.

It was confirmed that the compounds (1A)-101 and (1B)-101 were obtained by NMR measurement, UV-VIS absorption spectrum measurement, fluorescent light spectrum measurement, and IR measurement. For example, it was confirmed that a ratio of the number of H of an alkyl group:the number of H of a benzene ring, in $^1$H-NMR measurement is 276.0:36.9. Spectrum data of $^1$H-NMR at this time was illustrated in FIG. 7. The maximum absorption value ($\lambda_{max}$) was observed at a wavelength of 626 nm and 674 nm in a wavelength range of 500 nm to 800 nm, in the UV-VIS absorption spectrum measurement. In the fluorescent light spectrum measurement, a fluorescent light spectrum having the maximum value at a wavelength of 720 nm was observed. The compounds (1A)-101 and (1B)-101 show substantially the same light absorption characteristics and substantially the same light emission characteristics. It is considered that either of the compounds (1A)-101 and (1B)-101 has the above-described maximum absorption value and similar fluorescent light spectrum. FIG. 8 illustrates data of a UV-VIS absorption spectrum and a fluorescent light spectrum at this time. Among graphs in FIG. 8, a longitudinal axis on the left side indicates the scale of absorbance and a longitudinal axis on the right side indicates the scale of fluorescent intensity. FIG. 9 illustrates spectrum data of IR.

[Chem. 19]

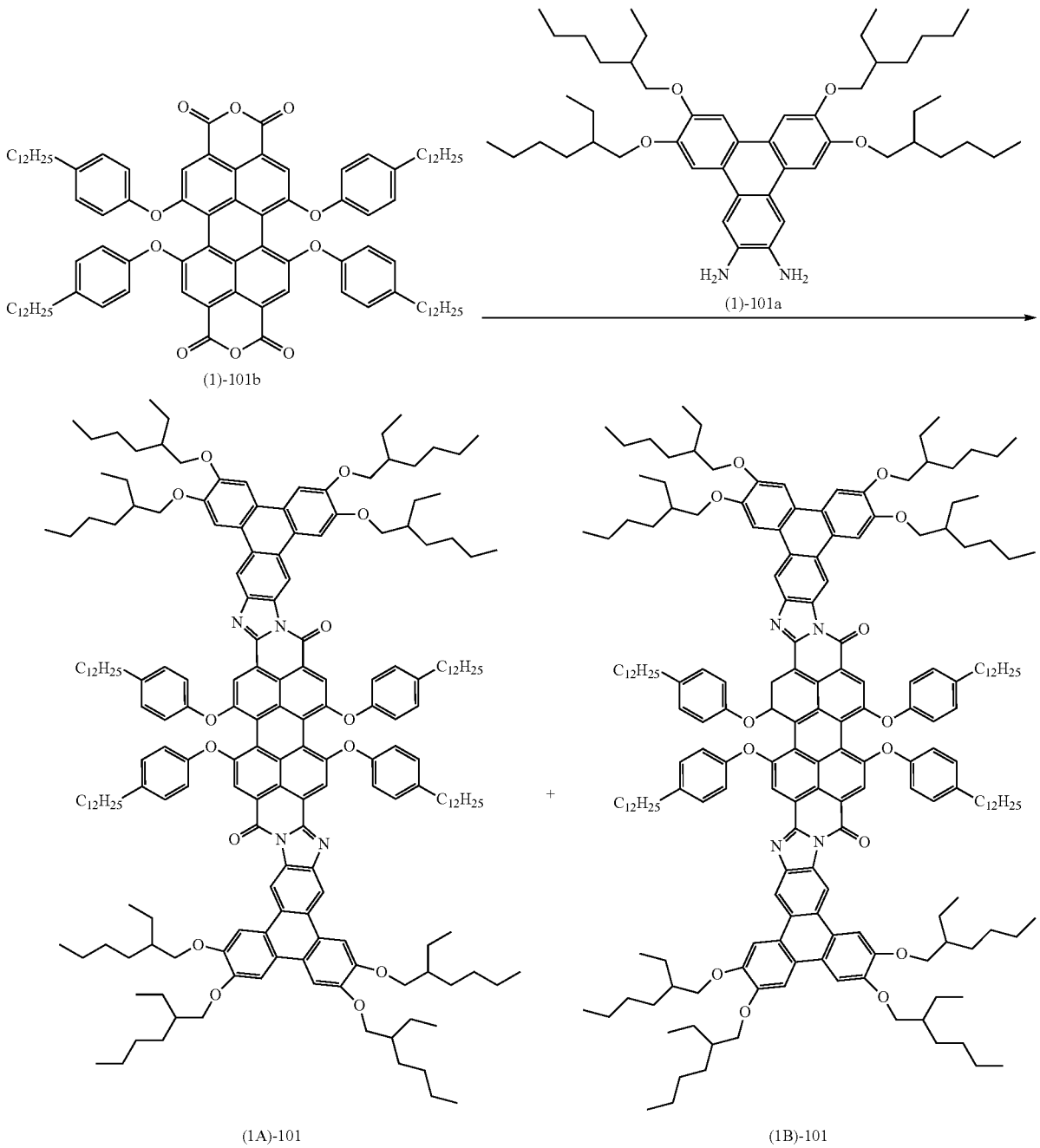

The compound (1A)-101 has a light absorption peak wavelength of 626 nm and 674 nm and can absorb light having sufficiently long wavelength. A peak wavelength of emitted light is 720 nm and emission light (fluorescence) has sufficiently long wavelength. The fluorescence quantum yield is 10%.

A light absorption peak wavelength of the compound (1A)-101 is 696 nm, which has been obtained by an expression of B3LYP/6-31+g(d) and by using Gaussian09 (manufactured by Gaussian Corporation). The obtained value was near to the experimental value.

Example 2

Compounds represented by the following formulas (1A)-102 and (1B)-102 (below, respectively abbreviated to a "compound (1A)-102" and a "compound (1B)-102") are manufactured as the compound (I) by using the similar method to that in Example 1 except that a compound represented by following formula (1)-102a is used as the compound (Ia) instead of the compound (1)-101a.

A light absorption peak wavelength of the compounds (1A)-102 and (1B)-102 is 696 nm, which has been obtained by an expression of B3LYP/6-31+g(d) and by using Gaussian09 (manufactured by Gaussian Corporation).

[Chem. 20]

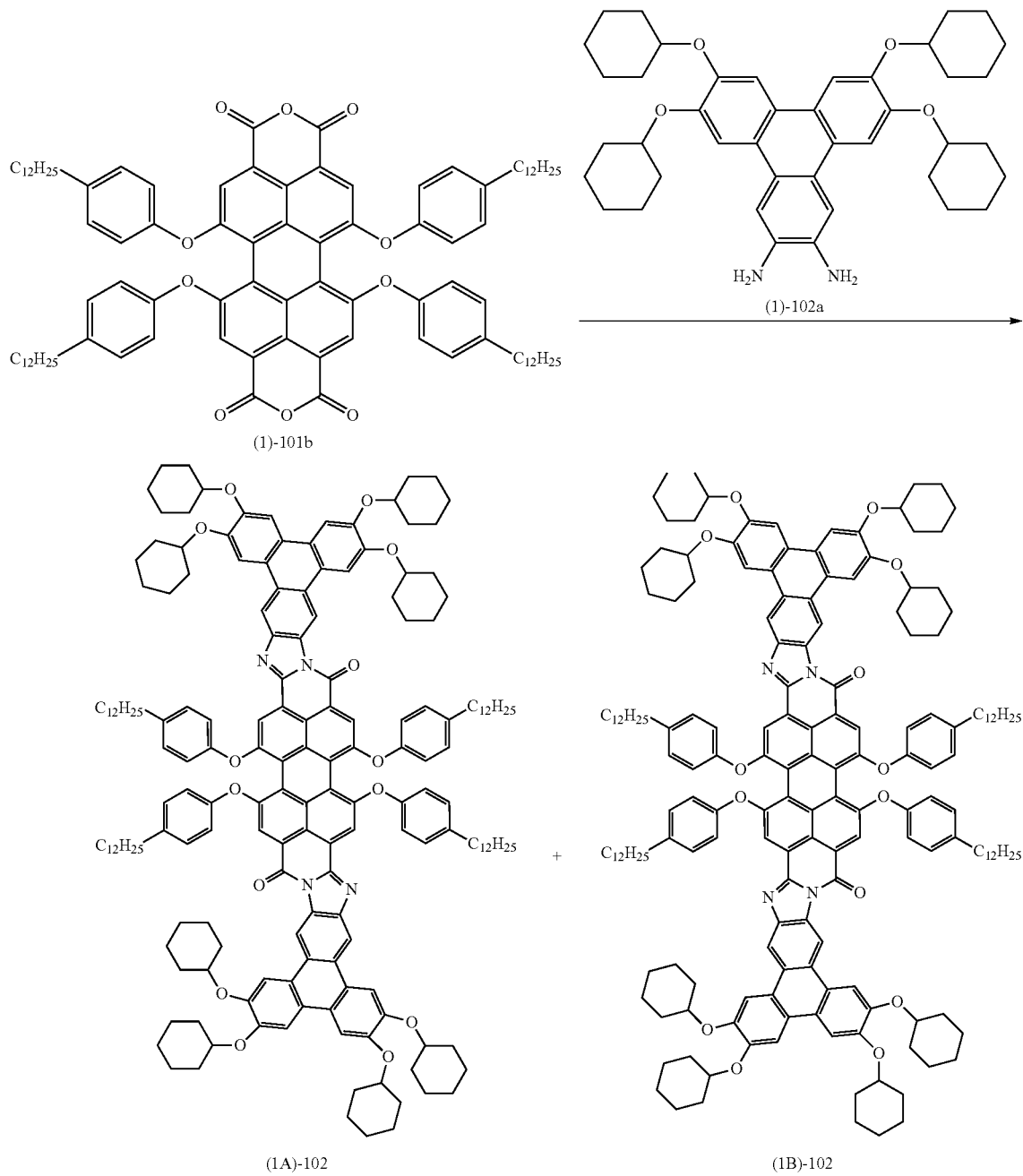

The compound (1)-102a is manufactured by using the similar method to a case of the compound (1)-101a except that cyclohexyl bromide is used instead of 1-bromo-2-ethyl hexane in the compound (Iab) manufacturing process (2).

Example 3

Compounds represented by the following formulas (1A)-103 and (1B)-103 (below, respectively abbreviated to a "compound (1A)-103" and a "compound (1B)-103") are manufactured as the compound (Ia) by using the similar method to that in Example 1 except that a compound represented by following formula (1)-103a is used as the compound (Ia) instead of the compound (1)-101a.

A light absorption peak wavelength of the compounds (1A)-103 and (1B)-103 is 696 nm, which has been obtained by an expression of B3LYP/6-31+g(d) and by using Gaussian09 (manufactured by Gaussian Corporation).

The compound (1)-103a is manufactured by using the similar method as a case of the compound (1)-101a except that the compound (1)-101abb obtained in the compound (Iabb) manufacturing process is used instead of the compound (1)-101ab in the compound (Iaa) manufacturing process, without performing of the compound (Iaba) manufacturing process and the compound (Iab) manufacturing process (2).

Manufacturing of Solar Cell Module

Example 4

The solar cell module 1 illustrated in FIGS. 1 to 3 is manufactured by using the compounds (I) according to Examples 1 to 3 individually as the phosphor 8.

[Chem. 21]

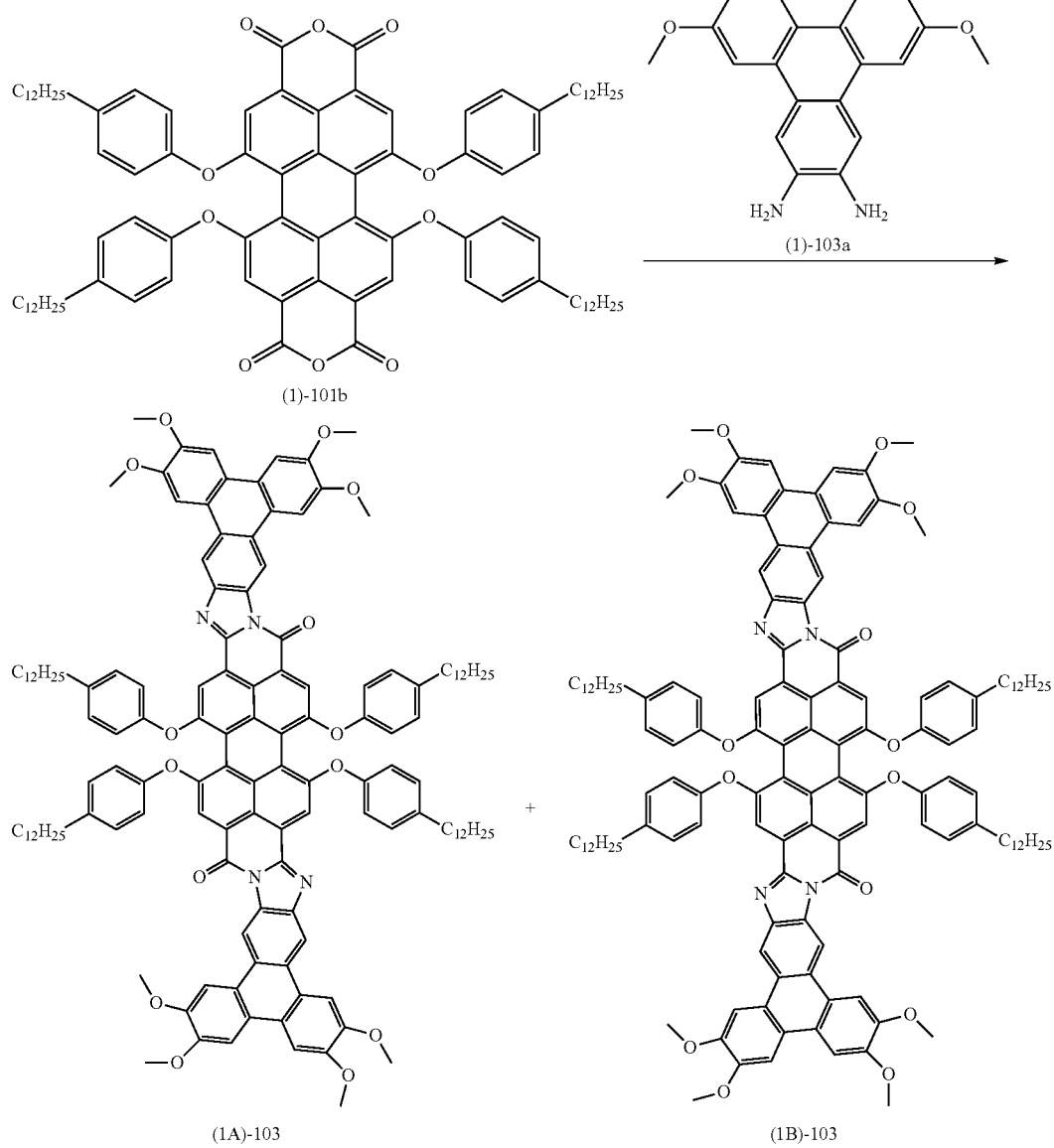

Example 5

The solar cell module 1 illustrated in FIGS. 1 to 3 is manufactured by using the compounds (I) according to Examples 1 to 3 individually as the phosphor 8 along with another phosphor other than the compound (I).

INDUSTRIAL APPLICABILITY

The present invention may be used in the solar cell module and the photovoltaic power generation device.

REFERENCE SIGNS LIST

- 1, 1001 SOLAR CELL MODULE
- 2, 28, 30, 1002 LIGHT CONCENTRATING PLATE (LIGHT GUIDE)
- 2a, 28a PRINCIPAL PLANE (LIGHT INCIDENT SURFACE) OF LIGHT CONCENTRATING PLATE
- 2b FIRST END FACE (LIGHT EXIT SURFACE) OF LIGHT CONCENTRATING PLATE
- 3, 1003 SOLAR CELL ELEMENT
- 7 TRANSPARENT SUBSTRATE
- 8 PHOSPHOR (COMPOUND (I))
- 26 FLUORESCENT LAYER
- 1000 PHOTOVOLTAIC POWER GENERATION DEVICE
- L SUNLIGHT
- L1 INCIDENT LIGHT

The invention claimed is:

1. A compound represented by the following general formula (IA) or (IB)

[Chem. 1]

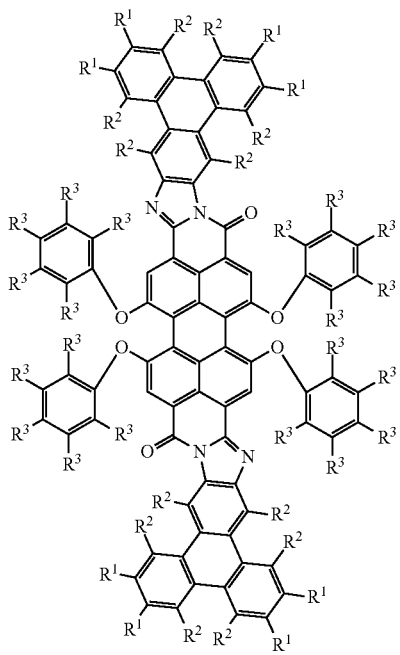

(IA)

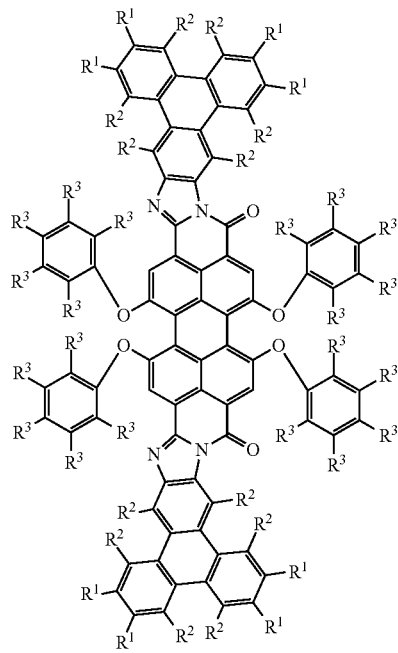

(IB)

(in the formula, $R^1$ and $R^2$ are each independently a hydrogen atom, an alkyl group, an alkoxy group, an aryl group, or an aryloxy group, and a plurality of the $R^1$ and the $R^2$ may be the same as each other or different from each other; $R^3$ corresponds to a hydrogen atom or an alkyl group, and a plurality of $R^3$ may be the same as each other or different from each other).

2. The compound according to claim 1, wherein
the $R^1$ and the $R^2$ are each independently a hydrogen atom, a 1C to 22C alkyl group, a 1C to 22C alkoxy group, a 6C to 22C aryl group, or a 6C to 22C aryloxy group, and
the $R^3$ is a hydrogen atom, or a 1C to 22C alkyl group.

3. The compound according to claim 2, wherein
the $R^1$ and the $R^2$ are each independently a hydrogen atom, a 1C to 18C alkyl group, a 1C to 18C alkoxy group, a 6C to 10C aryl group, or a 6C to 10C aryloxy group, and
the $R^3$ is a hydrogen atom, or a 6C to 18C alkyl group.

4. The compound according to claim 1, wherein
all of the $R^1$ are groups other than a hydrogen atom.

5. A solar cell module comprising the compound according to claim 1.

6. The solar cell module according to claim 5 comprising:
a light guide that has a light incident surface and a light exit surface having an area smaller than the light incident surface; and
a solar cell element that receives exiting light from the light exit surface so as to generate electrical power,
wherein the light guide contains the compound, and uses emission light from the compound, which is resulted from absorption of incident light from the light incident surface by the compound, as the exiting light.

7. A photovoltaic power generation device comprising:
the solar cell module according to claim 5.

* * * * *